(12) United States Patent
Sato et al.

(10) Patent No.: US 10,624,889 B2
(45) Date of Patent: Apr. 21, 2020

(54) INJECTABLE FORMULATION

(71) Applicant: OTSUKA PHARMACEUTICAL CO., LTD., Tokyo (JP)

(72) Inventors: Tetsuya Sato, Osaka (JP); Takuya Minowa, Osaka (JP); Yusuke Hoshika, Osaka (JP); Hidekazu Toyofuku, Osaka (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 0 days.

(21) Appl. No.: 15/702,361

(22) Filed: Sep. 12, 2017

(65) Prior Publication Data
US 2018/0092910 A1 Apr. 5, 2018

Related U.S. Application Data

(63) Continuation of application No. 14/395,681, filed as application No. PCT/JP2013/061950 on Apr. 23, 2013.

(60) Provisional application No. 61/636,932, filed on Apr. 23, 2012, provisional application No. 61/791,896, filed on Mar. 15, 2013.

(51) Int. Cl.
| | |
|---|---|
| *A61K 31/496* | (2006.01) |
| *A61K 47/10* | (2017.01) |
| *A61K 9/00* | (2006.01) |
| *A61K 47/18* | (2017.01) |
| *A61K 47/26* | (2006.01) |
| *A61K 47/02* | (2006.01) |
| *A61K 47/34* | (2017.01) |
| *A61K 9/10* | (2006.01) |
| *A61K 47/20* | (2006.01) |
| *A61K 47/24* | (2006.01) |

(52) U.S. Cl.
CPC .......... *A61K 31/496* (2013.01); *A61K 9/0019* (2013.01); *A61K 9/10* (2013.01); *A61K 47/02* (2013.01); *A61K 47/10* (2013.01); *A61K 47/183* (2013.01); *A61K 47/20* (2013.01); *A61K 47/24* (2013.01); *A61K 47/26* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 6,274,634 B1 | 8/2001 | Yasueda et al. | |
| 6,656,505 B2 * | 12/2003 | Kundu | A61K 9/0095 424/489 |
| 7,807,680 B2 | 10/2010 | Kostanski | |
| 8,030,313 B2 | 10/2011 | Kostanski | |
| 8,617,606 B2 | 12/2013 | Hiraoka et al. | |
| 8,722,679 B2 | 5/2014 | Kostanski | |
| 8,952,013 B2 | 2/2015 | Kostanski | |
| 9,457,026 B2 | 10/2016 | Hiraoka et al. | |
| 9,499,525 B2 | 11/2016 | Yamashita | |
| 2001/0036966 A1 | 11/2001 | Yasueda et al. | |
| 2003/0008010 A1 | 1/2003 | Yasueda et al. | |
| 2003/0195179 A1 | 10/2003 | Sawa | |
| 2005/0148597 A1 * | 7/2005 | Kostanski | A61K 9/0019 514/253.07 |
| 2009/0143403 A1 * | 6/2009 | Brown | A61K 9/0019 514/253.07 |
| 2009/0148529 A1 | 6/2009 | Hiraoka et al. | |
| 2009/0253807 A1 | 10/2009 | Sawa | |
| 2010/0029714 A1 | 2/2010 | Masuda | |
| 2010/0125060 A1 * | 5/2010 | Razzak | A61K 9/0019 514/210.05 |
| 2010/0179322 A1 * | 7/2010 | Yamashita | C07D 409/12 544/363 |
| 2010/0196486 A1 | 8/2010 | Hiraoka et al. | |
| 2011/0152286 A1 | 6/2011 | Yamashita et al. | |
| 2012/0091022 A1 * | 4/2012 | Nakagawa | A61K 31/496 206/438 |
| 2015/0087655 A1 | 3/2015 | Yamashita et al. | |
| 2015/0093442 A1 | 4/2015 | Kaneko et al. | |

(Continued)

FOREIGN PATENT DOCUMENTS

| | | |
|---|---|---|
| CN | 101442986 A | 5/2009 |
| CN | 101801342 A | 8/2010 |

(Continued)

OTHER PUBLICATIONS

Extended European Search Report for corresponding EP Application No. 13781456.8 dated Nov. 9, 2015.

(Continued)

*Primary Examiner* — Susan T Tran
*Assistant Examiner* — William Craigo
(74) *Attorney, Agent, or Firm* — Finnegan, Henderson, Farabow, Garrett & Dunner, LLP

(57) ABSTRACT

An object of the present invention is to provide a sustained-release injectable preparation which is in a medication administration form that can provide the effect of 7-[4-(4-benzo[b]thiophen-4-yl-piperazin-1-yl)butoxy]-1H-quinolin-2-one for a prolonged period of time, the preparation releasing a therapeutically effective amount of 7-[4-(4-benzo[b]thiophen-4-yl-piperazin-1-yl)butoxy]-1H-quinolin-2-one for at least one week. The present invention provides an injectable preparation containing 7-[4-(4-benzo[b]thiophen-4-yl-piperazin-1-yl)butoxy]-1H-quinolin-2-one or a salt thereof as an active ingredient, which releases the active ingredient in such a manner that its blood concentration is maintained for at least one week.

13 Claims, 15 Drawing Sheets

(56) References Cited

U.S. PATENT DOCUMENTS

2017/0035752 A1 2/2017 Hiraoka et al.
2018/0185358 A1 7/2018 Hiraoka et al.

FOREIGN PATENT DOCUMENTS

| JP | 11-29463 | 2/1999 |
|---|---|---|
| JP | 2006-316052 | 11/2006 |
| JP | 2007-501236 A | 1/2007 |
| JP | 2009-508859 A | 3/2009 |
| JP | 2010-507566 | 3/2010 |
| WO | WO 02/15878 A1 | 2/2002 |
| WO | WO 2005/016262 A2 | 2/2005 |
| WO | WO 2007/035348 A2 | 3/2007 |
| WO | WO 2008/050896 A1 | 5/2008 |
| WO | WO 2012/026562 A1 | 3/2012 |
| WO | WO 2012/129156 A1 | 9/2012 |
| WO | WO 2013/142205 A1 | 9/2013 |
| WO | WO 2013/162046 A1 | 10/2013 |
| WO | WO 2013/162048 A1 | 10/2013 |

OTHER PUBLICATIONS

International Search Report from the Japanese Patent Office for International Application No. PCT/JP2013/061950 dated Jul. 16, 2013.
JP Office Action dated Jan. 24, 2017 for corresponding Japanese Patent Application No. 2014-512621.
Kulshreshtha et al., Pharmaceutical Suspensions From Formulation Development to Manufacturing. p. 112 (Springer 2010).
Kulshreshtha et al., Pharmaceutical Suspensions From Formulation Development to Manufacturing, p. 113 (Springer 2010).
Office Action dated Dec. 9, 2015 for Colombian Patent Application No. 14-255947.
Office Action dated Jun. 27, 2016 for Colombian Patent Application No. 14-255947.
Reddy et al. In Pharmaceutical Suspension from formulation development to manufacturing, Wall et al. Eds., Springer, New York, 2010, Chapter 2, pp. 54-58.
Industrial Pharmaceutics, China Medical Science Press, 2010, $2^{nd}$ edition, pp. 182-185.
Pharmaceutics, People's Medical Publishing House, 1996, $3^{rd}$ edition, p. 97.
Pharmaceutics, People's Medical Publishing House, 1999, $4^{th}$ edition, p. 232.
Office Action dated Jun. 6, 2018 for corresponding CN Patent Application No, 201380021612.2.
Decision of Reexamination for corresponding CN Patent Application No. 201380021612.2 dated Jan. 18, 2019.
Industrial Pharmacy, Higher Education Press, $1^{st}$ edition, p. 166, Aug. 2006.
Office Action dated Dec. 30, 2019, for the corresponding Chinese Patent Application No. 201710701596.1.

* cited by examiner

INJECTABLE FORMULATION

This is a continuation of application Ser. No. 14/395,681, filed Oct. 20, 2014, which is the National Stage of PCT/JP2013/061950, filed Apr. 23, 2013, and claims benefit to Provisional Application No. 61/636,932, filed Apr. 23, 2012 and Provisional Application No. 61/791,896, filed Mar. 15, 2013, all of which are incorporated herein by reference.

TECHNICAL FIELD

The present invention relates to an injectable preparation comprising 7-[4-(4-benzo[b]thiophen-4-yl-piperazin-1-yl)butoxy]-1H-quinolin-2-one or a salt thereof.

BACKGROUND ART

7-[4-(4-Benzo[b]thiophen-4-yl-piperazin-1-yl)butoxy]-1H-quinolin-2-one (hereinafter also referred to as "Compound (I)") is a benzothiophene compound represented by Formula (I):

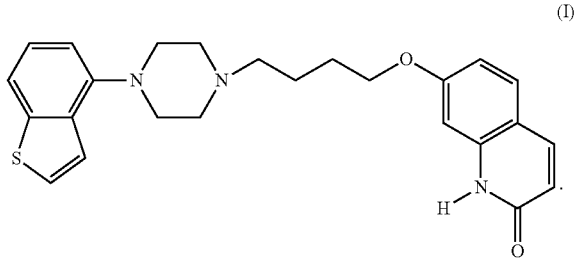 [SMILES: O=c1ccc2ccc(OCCCCN3CCN(c4cccc5sccc45)CC3)cc2[nH]1]

Compound (I) or salts thereof are known to have serotonin uptake inhibitory activity (or serotonin re-uptake inhibitory activity) in addition to dopamine $D_2$ receptor partial agonistic activity ($D_2$ receptor partial agonistic activity), serotonin 5-$HT_{2A}$ receptor antagonistic activity (5-$HT_{2A}$ receptor antagonistic activity), and adrenaline $\alpha_1$ receptor antagonistic activity ($\alpha_1$ receptor antagonistic activity) (Patent Literature (PTL) 1). Compound (I) and salts thereof have a wide therapeutic spectrum for central nervous system diseases (particularly schizophrenia).

CITATION LIST

Patent Literature

PTL 1: JP2006-316052A

SUMMARY OF INVENTION

Technical Problem

In central nervous system diseases such as schizophrenia, a long-acting medication administration form is useful because it increases patient compliance, and thereby lowers the relapse rate during treatment.

An object of the present invention is to provide an injectable preparation that exhibits the effect of Compound (I) or a salt thereof for a prolonged period of time, is stable even after long-term storage, and can be easily injected. The present invention provides a sustained-release injectable preparation that preferably maintains an effective blood concentration of Compound (I) or a salt thereof for at least one week.

Solution to Problem

The present inventors conducted extensive research to achieve the above object, and as a result, they found that an injectable preparation having a specific composition comprising Compound (I) or a salt thereof as an active ingredient does not form a hard cake even when Compound (I) precipitates, and can be easily re-dispersed by using a simple operation such as gentle stirring, and suitably injected. The inventors further found that the injectable preparation having the specific composition can exhibit the effect of Compound (I) or a salt thereof for a prolonged period of time. In particular, the inventors found that the injectable preparation can release a therapeutically effective amount of Compound (I) or a salt thereof for at least one week. The present invention has been accomplished upon further study based on this finding, and includes the inventions listed below.

Item 1. An aqueous suspension comprising secondary particles formed by the aggregation of particles (primary particles) of 7-[4-(4-benzo[b]thiophen-4-yl-piperazin-1-yl)butoxy]-1H-quinolin-2-one or a salt thereof, the secondary particles having a mean particle diameter (a mean secondary particle diameter) of 1 to 50 µm and being contained in a dispersed state.

Item 2. The aqueous suspension according to item 1, wherein the particles of 7-[4-(4-benzo[b]thiophen-4-yl-piperazin-1-yl)butoxy]-1H-quinolin-2-one or a salt thereof have a mean primary particle diameter of 0.1 to 20 µm.

Item 3. The aqueous suspension according to item 1 or 2, comprising 7-[4-(4-benzo[b]thiophen-4-yl-piperazin-1-yl)butoxy]-1H-quinolin-2-one in an amount of 0.1 to 40 wt %.

Item 4. An injectable preparation comprising the aqueous suspension according to any one of items 1 to 3.

Item 5. An injectable preparation comprising 7-[4-(4-benzo[b]thiophen-4-yl-piperazin-1-yl)butoxy]-1H-quinolin-2-one or a salt thereof, a particle binder, and water for injection, the particle binder being at least one member selected from the group consisting of sodium chloride, polyoxyethylene sorbitan fatty acid esters, block copolymers of ethylene oxide and propylene oxide, polyethylene glycols, tocopherol, tocotrienol and esters thereof, tocopherol acetate, tocopherol succinate, benzyl alcohol, poorly water-soluble polyoxyethylene diol dibenzoate, poorly water-soluble polyoxyethylene diol dimethylsulfonic acid and esters thereof, and benzyl benzoate.

Item 6. The injectable preparation according to item 5, wherein the 7-[4-(4-benzo[b]thiophen-4-yl-piperazin-1-yl)butoxy]-1H-quinolin-2-one or a salt thereof forms secondary particles and the secondary particles have a mean secondary particle diameter of 1 to 50 µm.

Item 7. The injectable preparation according to item 5 or 6, comprising a suspension of the 7-[4-(4-benzo[b]thiophen-4-yl-piperazin-1-yl)butoxy]-1H-quinolin-2-one or a salt thereof in water for injection.

Item 8. The injectable preparation according to item 5 or 6, comprising a precipitate of the 7-[4-(4-benzo[b]thiophen-4-yl-piperazin-1-yl)butoxy]-1H-quinolin-2-one or a salt thereof.

Item 9. The injectable preparation according to any one of items 5 to 8, wherein the particle binder is at least one member selected from the group consisting of sodium chloride, polyoxyethylene (20) sorbitan oleate, polyoxyethylene (160) polyoxypropylene (30) glycol, polyethylene glycols having an average molecular weight of 200 to 6,000, benzyl alcohol, and benzyl benzoate.

Item 10. The injectable preparation according to any one of items 4 to 9, having a pH of 5 to 8.

Item 11. The injectable preparation according to any one of items 4 to 10, which is for treating or preventing relapse of schizophrenia, bipolar disorder, or depression.
Item 12a. The aqueous suspension according to any one of items 1 to 3, wherein the 7-[4-(4-benzo[b]thiophen-4-yl-piperazin-1-yl)butoxy]-1H-quinolin-2-one or a salt thereof is a dihydrate of 7-[4-(4-benzo[b]thiophen-4-yl-piperazin-1-yl)butoxy]-1H-quinolin-2-one.
Item 12b. The injectable preparation according to any one of items 4 to 11, wherein the 7-[4-(4-benzo[b]thiophen-4-yl-piperazin-1-yl)butoxy]-1H-quinolin-2-one or a salt thereof is a dihydrate of 7-[4-(4-benzo[b]thiophen-4-yl-piperazin-1-yl)butoxy]-1H-quinolin-2-one.
Item 13a. The aqueous suspension according to claim 12a, comprising at least one member selected from the group consisting of polyoxyethylene sorbitan fatty acid esters and polyethylene glycols as a particle binder.
Item 13b. The injectable preparation according to claim 12b, comprising at least one member selected from the group consisting of polyoxyethylene sorbitan fatty acid esters and polyethylene glycols as a particle binder.
Item 14. A prefilled syringe that is prefilled with the injectable preparation according to any one of items 4 to 11, 12b, and 13b.
Item A. An injectable preparation comprising 7-[4-(4-benzo[b]thiophen-4-yl-piperazin-1-yl)butoxy]-1H-quinolin-2-one or a salt thereof as an active ingredient, the preparation releasing the active ingredient in such a manner that its therapeutically effective blood concentration is maintained for at least one week.
Item B. The injectable preparation according to item A, further comprising a binder.
Item C. The injectable preparation according to item A or B, having a pH of 5 to 8.

The injectable preparation of the present invention contains Compound (I) or a salt thereof as an active ingredient. Because the injectable preparation has a specific composition comprising Compound (I) or a salt thereof as an active ingredient, the active ingredient can be easily redispersed even when precipitation occurs, and can thus be restored to a state suitable for injection. Further, an effective blood concentration of Compound (I) or a salt thereof can be maintained for at least one week. The injectable preparation of the present invention is used in the form of a suspension including water for injection when administered.

In the injectable preparation of the present invention, Compound (I) or a salt thereof forms secondary particles and the secondary particles preferably have a mean particle diameter (a mean secondary particle diameter) of 1 to 50 µm. Preferably, (particularly before administration), the second particles are suspended in the injectable preparation.

One preferred mode of the injectable preparation of the present invention is an injectable preparation comprising an aqueous suspension containing secondary particles formed by the aggregation of particles (primary particles) of Compound (I) or a salt thereof, the secondary particles preferably having a mean particle diameter (a mean secondary particle diameter) of 1 to 50 µm and the secondary particles being suspended.

The secondary particles more preferably have a mean particle diameter (a mean secondary particle diameter) of 2 to 30 µm, still more preferably 3 to 20 µm, even more preferably 4 to 17 µm, yet more preferably 5 to 15 µm, and particularly preferably 5 to 12 µm.

Because the injectable preparation of the present invention is prepared by suspending a specific component that is either 7-[4-(4-benzo[b]thiophen-4-yl-piperazin-1-yl)butoxy]-1H-quinolin-2-one (Compound (I)) or a salt thereof in water and further adding a specific particle binder, primary particles of Compound (I) or a salt thereof can advantageously form secondary particles, and the preparation can advantageously contain in a stable manner secondary particles of Compound (I) or a salt thereof having such a mean secondary particle diameter. The specific particle binder as used herein means a component that can aggregate particles (primary particles) of Compound (I) or a salt thereof to form secondary particles.

In general, when a poorly water-soluble compound is suspended in water and left for a long period of time, particles of the compound often precipitate and solidify firmly (specifically, form a hard cake). Once such a hard cake has been formed in an injectable preparation prepared by suspending a poorly water-soluble active ingredient in water, resuspending the active ingredient is difficult. If the active ingredient cannot be suspended, problems such as inability to inject a sufficient amount of the active ingredient and undesirably lowered syringability arise. Therefore, preventing hard cake formation is an important issue in injectable preparations.

As explained in detail below, the injectable preparation of the present invention does not form a hard cake, even when Compound (I) or a salt thereof precipitates. By using a simple operation such as gentle stirring, the particles are easily resuspended advantageously. Although a restrictive interpretation is not desired, the advantageous effect of the injectable preparation of the present invention is presumably provided based on the following mechanism. Because the injectable preparation of the present invention is prepared by suspending a specific component that is either 7-[4-(4-benzo[b]thiophen-4-yl-piperazin-1-yl)butoxy]-1H-quinolin-2-one or a salt thereof in water and further adding a specific particle binder, particles of Compound (I) or a salt thereof aggregate to form secondary particles; therefore, even if Compound (I) or a salt thereof precipitates, it is difficult for the particles to be in a very closely packed state. The present invention includes injectable preparations comprising secondary particles of Compound (I) or a salt thereof in a precipitated state.

The secondary particles of Compound (I) or a salt thereof having the mean secondary particle diameter mentioned above can be produced, for example, by dispersing Compound (I) or a salt thereof having a mean primary particle diameter of about 0.1 to 20 µm, more preferably about 1 to 10 µm, and even more preferably about 2 to 5 µm, together with a vehicle as described below, in water for injection. When a bulk powder of Compound (I) or a salt thereof having the above mean primary particle diameter and a specific particle binder are used and formulated into an aqueous suspension (an injectable preparation), the particles aggregate to the desired mean particle diameter, and the aggregated secondary particles of Compound (I) or a salt thereof can be well dispersed.

The term "mean particle diameter" as used herein refers to volume mean diameter as measured by using a laser diffraction-scattering method. Particle size distribution is measured by using a laser diffraction-scattering method, and the mean particle diameter is calculated from the particle size distribution.

Stated more specifically, the term "mean primary particle diameter" refers to a volume mean diameter value calculated from the particle size distribution measured by using a laser diffraction scattering method while circulating an aqueous suspension under ultrasonic irradiation using a circulation cell and using water as a medium. The term "secondary particle diameter" as used herein refers to a volume mean diameter value calculated from the particle size distribution measured by using a laser diffraction scattering method while circulating the aqueous suspension using a circulation cell and using water as a medium (without ultrasonic irradiation).

Examples of particle binders that can be used in the present invention include aqueous particle binders such as sodium chloride, polyoxyethylene sorbitan fatty acid esters, polyethylene glycols, block copolymers of ethylene oxide and propylene oxide; and oily particle binders such as tocopherol, tocotrienol and esters thereof, tocopherol acetate, tocopherol succinate, benzyl alcohol, poorly water-soluble polyoxyethylene diol dibenzoate, poorly water-soluble polyoxyethylene diol dimethylsulfonic acid and esters thereof, benzyl benzoate, and like benzoic acid esters.

"Fatty acids" of polyoxyethylene sorbitan fatty acid esters are preferably fatty acids having 12 to 18 carbon atoms, and more preferably having 16 to 18 carbon atoms. Specific examples include lauric acid, myristic acid, palmitic acid, stearic acid, oleic acid, linoleic acid, and the like. Oleic acid is particularly preferable. Among polyoxyethylene sorbitan fatty acid esters, polyoxyethylene (20) sorbitan laurate, polyoxyethylene (20) sorbitan stearate, and polyoxyethylene (20) sorbitan oleate are preferable. Specific examples include Polysorbate 20, Polysorbate 60, and Polysorbate 80. Polyoxyethylene (20) sorbitan oleate is particularly preferable.

The polyethylene glycol preferably has an average molecular weight of about 200 to 6,000. Specific examples of such polyethylene glycols include macrogol 400, macrogol 4000, and the like.

The block copolymer of ethylene oxide and propylene oxide (also referred to as EO/PO block random copolymer) preferably contains ethylene oxide at a higher polymerization weight ratio relative to propylene oxide. In particular, polyoxyethylene (160) polyoxypropylene (30) glycols (such as Pluronic F68) are preferable. Such particle binders may be used singly or in a combination of two or more. When two or more types of binders are used, either two or more types of binders selected from aqueous particle binders or two or more types of binders selected from oily particle binders are preferably used. It is preferable to use either aqueous particle binders alone or oily particle binders alone.

In particular, it is preferable to use at least one particle binder selected from the group consisting of sodium chloride, polyoxyethylene sorbitan fatty acid esters (in particular, polyoxyethylene (20) sorbitan oleate), polyethylene glycols, block copolymers of ethylene oxide and propylene oxide (in particular, polyoxyethylene (160) polyoxypropylene (30) glycol), benzyl alcohol, and benzyl benzoate. More preferable is the use of at least sodium chloride, polyoxyethylene (20) sorbitan oleate, polyethylene glycols having an average molecular weight of 200 to 6,000, polyoxyethylene (160) polyoxypropylene (30) glycol, or benzyl benzoate.

Among these, sodium chloride can particularly advantageously aggregate Compound (I) or a salt thereof to a secondary particle diameter, and can stably maintain secondary particles. Further, sodium chloride can function as an isotonizing agent as described below. Therefore, the use of sodium chloride is particularly preferable.

Further, polyoxyethylene sorbitan fatty acid esters, polyethylene glycols, and block copolymers of ethylene oxide and propylene oxide are preferable because these compounds have an effect of improving syringability of the injectable preparation.

The concentration of the specific particle binder used in the present invention may vary depending on the type of particle binder used. For example, the particle binder is preferably contained in the injectable preparation in a concentration of about 0.01 to 500 mg/mL, more preferably about 0.05 to 450 mg/mL, and even more preferably about 0.06 to 300 mg/mL. The particle binder is preferably contained in an amount of about 0.01 to 500 parts by weight, more preferably about 0.05 to 450 parts by weight, and even more preferably about 0.06 to 300 parts by weight, per 100 parts by weight of Compound (I) or a salt thereof.

The concentration of each component that can be used as a particle binder in the injectable preparation is described below.

Sodium chloride is preferably contained in the injectable preparation in a concentration of about 0.1 mg/mL or more, and more preferably 1 mg/mL or more. More specifically, sodium chloride is preferably contained in a concentration of about 0.1 to 400 mg/mL, more preferably about 1 to 200 mg/mL, still more preferably about 1 to 100 mg/mL, and still even more preferably about 1 to 50 mg/mL, and particularly preferably about 2 to 40 mg/mL. The amount of sodium chloride is preferably 1 to 100 parts by weight, more preferably 1 to 200 parts by weight, still more preferably 1 to 100 parts by weight, and still even more preferably 1 to 50 parts by weight, and particularly preferably 2 to 40 parts by weight, per 100 parts by weight of Compound (I) or a salt thereof.

Polyethylene glycol is preferably contained in the injectable preparation in a concentration of about 1 to 40 mg/mL, more preferably about 5 to 40 mg/mL, still preferably about 10 to 40 mg/mL, and yet preferably about 20 to 40 mg/mL. The amount of polyethylene glycol is preferably 1 to 40 parts by weight, more preferably 5 to 40 parts by weight, still more preferably 10 to 40 parts by weight, and yet preferably 20 to 40 parts by weight, per 100 parts by weight of Compound (I) or a salt thereof.

Polyoxyethylene sorbitan fatty acid ester is preferably contained in the injectable preparation in a concentration of about 0.01 to 10 mg/mL, more preferably about 0.1 to 5 mg/mL, still preferably about 0.1 to 1 mg/mL, and yet preferably about 0.2 to 0.5 mg/mL. The amount of polyoxyethylene sorbitan fatty acid ester is preferably 0.01 to 10 parts by weight, more preferably 0.1 to 5 parts by weight, still preferably 0.1 to 1 parts by weight, and yet preferably 0.2 to 0.5 part by weight, per 100 parts by weight of Compound (I) or a salt thereof.

Benzyl benzoate is preferably contained in the injectable preparation in a concentration of about 0.1 to 10 mg/mL, more preferably about 0.5 to 5 mg/mL, and still preferably about 0.5 to 3 mg/mL. The amount of benzyl benzoate is preferably 0.1 to 10 parts by weight, more preferably 0.5 to 5 parts by weight, and still preferably 0.5 to 3 parts by weight, per 100 parts by weight of Compound (I) or a salt thereof.

The term "100 parts by weight of Compound (I) or a salt thereof" as used herein refers to an amount of 100 parts by weight in terms of Compound (I), which is obtained by converting the amount of Compound (I) or a salt thereof contained in the injectable preparation to the amount of Compound (I).

The salt of Compound (I) is not particularly limited insofar as it is a pharmaceutically acceptable salt. Examples include alkali metal salts (e.g., sodium salts and potassium salts); alkaline earth metal salts (e.g., calcium salts and magnesium salts) and like metal salts; ammonium salts; alkali metal carbonates (e.g., lithium carbonate, potassium carbonate, sodium carbonate, and cesium carbonate); alkali metal hydrogen carbonates (e.g., lithium hydrogen carbonate, sodium hydrogen carbonate, and potassium hydrogen carbonate); alkali metal hydroxides (e.g., lithium hydroxide, sodium hydroxide, potassium hydroxide, and cesium hydroxide), and like salts of inorganic bases; tri(lower) alkylamines (e.g., trimethylamine, triethylamine, and N-ethyldiisopropylamine), pyridine, quinoline, piperidine, imidazole, picoline, dimethylaminopyridine, dimethylaniline, N-(lower)alkyl-morpholines (e.g., N-methylmorpholine), 1,5-diazabicyclo[4.3.0]nonene-5 (DBN), 1,8-diazabicyclo[5.4.0]undecene-7 (DBU), 1,4-diazabicyclo[2.2.2]octane (DABCO), and like salts of organic bases; hydrochloride, hydrobromate, hydroiodide, sulfate, nitrate, phosphate, and like salts of inorganic acids; and formate, acetate, propionate, oxalate, malonate, succinate, fumarate, maleate, lactate, malate, citrate, tartrate, carbonate, picrate, methanesulfonate, ethanesulfonate, p-toluenesulfonate, glutamate, pamoate, and like salts of organic acids. The term "(lower) alkyl" as used herein refers to an alkyl having 1 to 6 carbon atoms.

"Compound (I) or a salt thereof" includes an anhydride of Compound (I) or of a salt thereof, a solvate (e.g., a hydrate, preferably a dihydrate) of Compound (I) or of a salt thereof, various crystalline forms of such anhydrides and solvates, and mixtures thereof, unless otherwise specified. "Compound (I) or a salt thereof" is preferably an anhydride of Compound (I) or of a salt thereof, or a hydrate of Compound (I) or of a salt thereof, more preferably a hydrate of Compound (I) or of a salt thereof, and even more preferably a dihydrate of Compound (I) or of a salt thereof. The phrase "an anhydride of Compound (I) or of a salt thereof" means an anhydride of Compound (I) or an anhydride of a salt of Compound (I). The phrase "a solvate (e.g., a hydrate) of Compound (I) or of a salt thereof" means a solvate (e.g., a hydrate) of Compound (I) or a solvate (e.g., a hydrate) of a salt of Compound (I).

Compound (I) or a salt thereof can be used singly or in a combination of two or more (for example, as a mixture).

An anhydride of Compound (I) or of a salt thereof can be obtained, for example, by using the methods disclosed in Examples 1 and 42 to 47 of JP2006-316052A, the disclosure of which is incorporated herein by reference. A preferable example of a hydrate of Compound (I) or of a salt thereof is a dihydrate as described above. The dihydrate can be obtained, for example, by using a method comprising the steps of:

(1) mixing an acid (preferably at least one organic acid selected from the group consisting of acetic acid and lactic acid) and Compound (I) in an alcohol-water mixed solution (preferably a mixture of ethanol and water) to prepare an acidic mixed solution;
(2) cooling the solution obtained in the above step; and
(3) mixing the solution cooled in step (2) with an alkali (such as sodium hydroxide or potassium hydroxide) to adjust the pH to 7 or more.

More specifically, the dihydrate of Compound (I) can be produced, for example, by using the following production method (A) or (B).

Production Method (A) Comprises the Steps of:
(a1): mixing acetic acid and Compound (I) in an ethanol-water mixed solution to prepare an acidic solution;
(a2): cooling the solution obtained in step (a1) to 4° C. or lower; and
(a3): adjusting the cooled solution to a pH of 7 or more with an alkali, such as sodium hydroxide or potassium hydroxide.

Production Method (B) Comprises the Steps of:
(b1): mixing lactic acid and Compound (I) in an ethanol-water mixed solution to prepare an acidic mixed solution;
(b2): cooling the solution obtained in step (b1) to 4° C. or lower; and
(b3): adjusting the cooled solution to a pH of 7 or more with an alkali such as sodium hydroxide or potassium hydroxide.

The dihydrate of the benzothiophene compound of Formula (I) or of a salt thereof can be produced by using steps (1) to (3) described above. Step (1) may be a step (step (I')) in which an alcohol, water, at least one organic acid selected from the group consisting of acetic acid and lactic acid, and Compound (I) are mixed to prepare an acidic mixed solution. Particularly preferably, in step (1), at least one organic acid selected from the group consisting of acetic acid and lactic acid and an anhydride of the benzothiophene compound of Formula (I) are mixed in an ethanol-water mixed solution to prepare an acid solution. Lactic acid that is used as the organic acid may be D-form, L-form, or a mixture thereof.

The ethanol-water mixed solution used in step (1) is preferably prepared so as to contain ethanol in an amount of about 95 volume % or less, more preferably about 70 volume % or less, and even more preferably about 60 volume % or less. When the solution contains ethanol in an amount of 95 volume % or less, a dihydrate of Compound (I) can be obtained. Although the lower limit of the amount of ethanol in the solution is not particularly limited, it is preferably about 20 volume %, and more preferably about 30 volume %.

The concentration of the benzothiophene compound of Formula (I) in the ethanol-water mixed solution is preferably about 0.1 to 30 wt %, more preferably about 0.5 to 20 wt %, and even more preferably about 1 to 10 wt %. The expression "wt %" used herein refers to w/w %. When the concentration of the benzothiophene compound of Formula (I) is set to the above range, the benzothiophene compound of Formula (I) can be fully dissolved in the ethanol-water mixed solution, and a dihydrate with a higher purity can be obtained by performing the subsequent steps described below (steps (2) and (3)).

The amount of the organic acid in the ethanol-water mixed solution is not particularly limited insofar as the system can be adjusted to an acidic condition. For example, the organic acid is preferably contained in an amount of about 0.1 to 20 wt %, more preferably about 0.3 to 10 wt %, and even more preferably about 0.5 to 5 wt %, in the ethanol-water mixed solution.

The amount of the organic acid is not particularly limited insofar as the system can be adjusted to an acidic condition. For example, the organic acid is preferably contained in an amount of about 5 to 100 parts by weight, and more preferably about 20 to 80 parts by weight, based on 100 parts by weight of the benzothiophene compound of Formula (I).

The temperature at which the solution is prepared in step (1) is not particularly limited insofar as the following conditions are met: the benzothiophene compound of Formula (I) is dissolved in a liquid containing the above organic acid and ethanol-water mixed solution; ethanol, water, or the organic acid does not vaporize; and the benzothiophene compound of Formula (I) does not decompose. Specifically, the temperature is preferably about 50 to 120° C., and more preferably about 70 to 100° C. A reflux temperature (about 80° C.) may be used. Step (2) is a step in which the solution obtained in step (1) is cooled.

The cooling temperature is 5° C. or less, preferably about 0° C. or less, and more preferably about −2° C. or less. When the pH of the solution is adjusted with an alkali in the subsequent step, heat is generated. Therefore, when the cooling temperature is higher than 5° C., the yield of the dihydrate of the benzothiophene compound of Formula (I) or of a salt thereof tends to be insufficient. The lower limit of the cooling temperature in step (2) is not particularly limited. However, in view of the fact that the temperature must be raised in the subsequent step and that water may be frozen, the lower limit of the cooling temperature is preferably about −20° C., and more preferably about −10° C.

Step (3) is a step in which the solution cooled in step (2) is mixed with an alkali to adjust the pH to 7 or more. Examples of the alkali include sodium hydroxide, potassium hydroxide, and the like.

For mixing the solution cooled in step (2) with an alkali, an aqueous alkali solution prepared in advance may be used. The concentration of the aqueous alkali solution is, for example, about 0.1 to 25 wt %, and more preferably about 0.5 to 10 wt %.

To avoid a rapid temperature rise of the mixed solution in the system by the addition of an alkali (aqueous solution) as described above, the alkali (aqueous solution) is preferably pre-cooled. The temperature of the alkali (aqueous solution) is preferably about −5 to 15° C., and more preferably about −2 to 5° C.

The amount of alkali is not particularly limited insofar as the solution in the system can be adjusted to a pH of 7 or more. For example, an alkali is preferably added in an amount of about 0.3 to 10 parts by weight, and more preferably about 0.5 to 3 parts by weight, per part by weight of the organic acid incorporated in the solution in step (1).

In step (3), the solution is adjusted with an alkali to a pH of 7 or more, more preferably about 7.5 or more, and more preferably about 8 or more. When the pH is less than 7, the yield of the dihydrate of the benzothiophene compound of Formula (I) or of a salt thereof tends to be insufficient. Although the upper limit of the pH is not particularly limited, it is preferably, for example, a pH of about 12, and more preferably a pH of about 10, in view of facilitating washing the precipitated dihydrate of the benzothiophene compound of Formula (I), forming a salt of the benzothiophene compound, etc.

By performing steps (1) to (3), the dihydrate of the benzothiophene compound of Formula (I) or of a salt thereof is precipitated.

The precipitated dihydrate of the benzothiophene compound of Formula (I) or of a salt thereof is separated into solid and liquid phases by using a known method and purified by washing with water.

Preferably, the obtained dihydrate of the benzothiophene compound of Formula (I) is heated to about 10° C. or higher, and more preferably to about 10 to 50° C.

The physicochemical properties of the dihydrate of the benzothiophene compound of Formula (I) obtained by using the above production process are shown below.

X-Ray Powder Diffraction

The dihydrate of the benzothiophene compound of Formula (I) is identified by using an X-ray powder diffraction pattern measured by copper radiation of λ=1.5418 Å through a monochromator. The dihydrate of the benzothiophene compound of Formula (I) has peaks shown in FIG. 2 in the X-ray powder diffraction pattern, and has characteristic peaks at the following diffraction angles (2θ) in the X-ray powder diffraction pattern. These peaks are different from the peaks of the known benzothiophene compound of Formula (I) (in the form of an anhydride).

Diffraction Angles (2θ)
8.1°
8.9°
15.1°
15.6°
24.4°

The dihydrate of the benzothiophene compound of Formula (I) of the present invention has peaks at the following diffraction angles (2θ) as shown in FIG. 2, in addition to the above peaks.

Diffraction Angles (2θ)
11.6°, 12.2°, 14.0°, 16.3°, 18.1°, 18.4°, 18.9°, 19.5°, 20.5°, 21.5°, 22.6°, 23.3°, 25.0°, 26.1°, 26.4°, 27.1°, 28.1°, 28.5°, 28.9°, 29.8°, 30.4°, 30.7°, 31.6°, 32.9°, 33.9°, 34.4°, 35.2°, 36.0°, 36.7°, 37.4°, 38.3°.

Although the above diffraction angles (2θ) may contain an error of −0.2 to +0.2° according to the measuring instrument, measurement conditions, etc., such a level of error is within an acceptable range in the present invention.

Infrared Absorption Measurement

The dihydrate of the benzothiophene compound of Formula (I) is identified by using an infrared absorption spectrum measured by using the potassium bromide tablet method. In the infrared absorption spectrum, the dihydrate of the benzothiophene compound of Formula (I) has a spectrum as shown in FIG. 3 and has peaks at the following wavenumbers ($cm^{-1}$):

Wavenumbers
3509 $cm^{-1}$
2934 $cm^{-1}$
2812 $cm^{-1}$
1651 $cm^{-1}$
1626 $cm^{-1}$
1447 $cm^{-1}$
1223 $cm^{-1}$
839 $cm^{-1}$ The dihydrate of the benzothiophene compound of Formula (I) of the present invention has peaks at the wavenumbers shown in FIG. 3, in addition to the above peaks.

Although the wavenumbers ($cm^{-1}$) may contain an error of −0.5 to +0.5 $cm^{-1}$ according to the measuring instrument, measurement conditions, etc., such a level of error is within an acceptable range in the present invention.

The dihydrate of the benzothiophene compound of Formula (I) is identified by using a Raman spectrum. The dihydrate has the Raman spectrum shown in FIG. 4 and has peaks in the vicinity of the following wavenumbers ($cm^{-1}$):

Wavenumbers
1497 $cm^{-1}$
1376 $cm^{-1}$
1323 $cm^{-1}$
1311 $cm^{-1}$
1287 $cm^{-1}$
1223 $cm^{-1}$
781 $cm^{-1}$ The dihydrate has peaks in the vicinity of the following wavenumbers shown in FIG. 4, in addition to the above peaks:

Wavenumbers
1656 $cm^{-1}$, 1613 $cm^{-1}$, 1563 $cm^{-1}$, 1512 $cm^{-1}$, 1468 $cm^{-1}$, 1446 $cm^{-1}$, 1241 $cm^{-1}$, 1203 $cm^{-1}$, 1145 $cm^{-1}$, 1096 $cm^{-1}$, 1070 $cm^{-1}$, 971 $cm^{-1}$, 822 $cm^{-1}$ Water Content The dihydrate of the benzothiophene compound of Formula (I) contains water in an amount of 6.5 to 8.8 wt %, and more specifically 7.3 to 8.1 wt %. The water content is measured by using the Karl Fischer method.

¹H-NMR Measurement

The dihydrate of the benzothiophene compound of Formula (I) is identified according to peaks measured by ¹H-NMR spectroscopy. The dihydrate of the benzothiophene compound of Formula (I) has a ¹H-NMR spectrum as shown in FIG. 1 and has proton peaks in the ¹H-NMR spectrum measured in Production Example 1 below.

The injectable preparation preferably contains Compound (I) or a salt thereof in a proportion of about 0.1 to 40 wt %, more preferably about 1 to 20 wt %, and even more preferably about 5 to 15 wt %, based on the total weight of the injectable preparation. That is, Compound (I) or a salt thereof is preferably present in the injectable preparation in an amount of about 0.1 to 40% (w/v), more preferably about 1 to 20% (w/v), even more preferably about 2 to 15% (w/v), still more preferably about 5 to 15% (w/v), and particularly preferably about 5 to 11% (w/v), based on the total weight of the injectable preparation. More specifically, the injectable preparation preferably contains Compound (I) or a salt thereof in a concentration of, for example, about 1 to 400 mg/mL, more preferably about 10 to 200 mg/mL, even more preferably about 20 to 150 mg/mL, and still more preferably about 50 to 110 mg/mL.

The proportion and amount of Compound (I) or a salt thereof in the injectable preparation of the present invention are based on the proportion and amount of Compound (I).

In the production of an injectable preparation of the present invention that contains Compound (I) or a salt thereof in a relatively high concentration (specifically, 200 mg/mL or higher), it may be difficult to handle the injectable preparation because of its high viscosity (increased viscosity due to air bubble entrapment). In such a case, a defoaming step is preferably added to the production process. It is also preferable to use a suspending agent that suppresses viscosity, or, further, to use a water-repellent vial (in particular, a fluorine-coated water-repellent vial). Use of a water-repellent vial can enhance handling ease and reduce foaming.

The amount of Compound (I) or a salt thereof in the injectable preparation is preferably about 1 to 400 mg, more preferably about 10 to 200 mg, and even more preferably about 50 to 110 mg.

The bulk powder of Compound (I) or a salt thereof having the desired primary particle mean particle diameter can be produced by using a wet milling process, such as wet ball milling using media or wet milling without using media (e.g., a Manton-Gaulin homogenizer), or by using a dry milling process, such as jet milling. A freeze grinding method in liquid nitrogen or under freezing can also be used.

The wet milling process preferably uses wet ball milling. When the desired mean particle diameter of the primary particles of Compound (I) or a salt thereof is more than about 1 μm, the primary suspension (comprising a mixture of Compound (I) or a salt thereof with a vehicle) is passed through a wet ball mill a single time (single pass) at about 5 to 15 L/hr, preferably about 8 to 12 L/hr, and more preferably about 10 L/hr, to reduce the mean particle diameter of the primary particles to the desired range of, for example, about 1 to 5 μm.

In addition to ball mills (such as Dyno mills), other low-energy mills (such as roller mills) and high-energy mills may be used. Examples of usable high-energy mills include Netzsch mills, DC mills, and Planetary mills.

Other techniques for particle size reduction that may be used include aseptic controlled crystallization, high-shear homogenization, high-pressure homogenization, and microfluidization.

The injectable preparation of the present invention can stably contain secondary particles of Compound (I) or a salt thereof having the specific mean secondary particle diameter mentioned above.

With respect to an injectable preparation that comprises Compound (I) or a salt thereof as an active ingredient, the injectable preparation containing this active ingredient in the form of secondary particles having the specific secondary particle diameter mentioned above exhibits better sustained release properties (more specifically, excessive increase of blood concentration is not observed and the sustainability of the medicinal efficacy is equal or better) after administration, compared to an injectable preparation containing the same active ingredient in the form of primary particles.

Furthermore, the injectable preparation of the present invention comprising secondary particles of Compound (I) or a salt thereof having the specific mean secondary particle diameter mentioned above has the following property: when allowed to stand for a long period of time, the secondary particles precipitate but the precipitate does not solidify, and upon a simple operation such as gentle stirring or slight shaking with the hand, the secondary particles are easily suspended and revert to a suspension. Therefore, the injectable preparation of the present invention can be easily restored to a suspension from the precipitate that is formed after long-term storage, and the restored suspension as is can be preferably injected into a patient.

When precipitation occurs after being allowed to stand, the precipitation height (Rf value) is preferably 0.5 or more, more preferably 0.6 or more, still preferably 0.7 or more, and yet preferably 0.8 or more, with the height of the liquid surface defined as 1. The Rf value is measured after the injectable preparation is stirred well and allowed to stand at room temperature for at least five days. A larger Rf value is considered to indicate greater difficulty for the precipitated particles to be in a very closely packed state. Accordingly, a pharmaceutical preparation with a larger Rf value is most likely to have a high effect of preventing hard cake formation.

The injectable preparation of the present invention preferably has a relative osmotic pressure close to 1. More specifically, the injectable preparation preferably has a relative osmotic pressure of 1 to 2, more preferably 1 to 1.5, even more preferably 1 to 1.2, and still even more preferably 1 to 1.1.

The injectable preparation containing Compound (I) of the present invention or a salt thereof preferably comprises, in addition to Compound (I) or a salt thereof, a vehicle for Compound (I) or a salt thereof, and water for injection.

Examples of the vehicle for Compound (I) or a salt thereof include particle binders, dispersants (suspending agents), isotonizing agents, stabilizers, buffers, pH adjusters, solvents, and the like. In particular, as stated above, due to the specific particle binder contained in the injectable preparation of the present invention, Compound (I) or a salt thereof aggregates to form secondary particles, and the injectable preparation can advantageously contain the secondary particles in a stable manner. Therefore, the use of a specific particle binder is important. Other vehicles can be suitably added insofar as the effect of the present invention is not adversely affected.

Examples of dispersants (suspending agents) include sodium carboxymethyl cellulose, hydroxypropyl cellulose, carboxymethyl cellulose, hydroxypropyl ethylcellulose, hydroxypropyl methylcellulose, and Carbopol 934 (registered trademark) (manufactured by Union Carbide)), cetylpyridinium chloride, gelatin, casein, lecithin (phosphatide), dextran, glycerol, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, dodecyl trimethyl ammonium bromide, polyoxyethylene stearate, colloidal silicon dioxide, phosphate, sodium dodecyl sulfate, carboxymethylcellulose calcium, hydroxypropyl celluloses (e.g., HPC, HPC-SL, and HPC-L), methylcellulose, hydroxyethylcellulose, hydroxypropylcellulose, hydroxypropylmethylcellulose phthalate, non-crystalline cellulose, aluminum magnesium silicate, triethanolamine, polyvinyl alcohol (PVA), 4-(1,1,3,3-tetramethylbutyl)-phenol polymer with ethylene oxide and formaldehyde (also known as tyloxapol, superione, and triton); tetrafunctional block copolymers derived from sequential addition of propylene oxide and ethylene oxide to ethylenediamine (poloxamines) (e.g., Tetronic 908 (registered trademark), also known as Poloxamine 908 (registered trademark) (manufactured by BASF Wyandotte Corporation, Parsippany, N.J.)); charged phospholipids such as dimyristoyl phosphatidyl glycerol, dioctylsulfosuccinate (DOSS); Tetronic 1508 (registered trademark) (T-1508) (manufactured by BASF Wyandotte Corporation), dialkylesters of sodium sulfosuccinic acid (e.g., Aerosol OT (registered trademark), which is a dioctyl ester of sodium sulfosuccinic acid (manufactured by American Cyanamid)); Duponol P (registered trademark), which is sodium lauryl sulfate (manufactured by DuPont); Triton X-200 (registered trademark), which is an alkyl aryl polyether sulfonate (manufactured by Rohm and Haas); Crodestas F-110 (registered trademark), which is a mixture of sucrose stearate and sucrose distearate (manufactured by Croda Inc.); p-isononylphenoxypoly-(glycidol), also known as Olin-10G (registered trademark) or Surfactant 10-G (registered trademark) (manufactured by Olin Chemicals, Stamford, Conn.); Crodestas SL-40 (manufactured by Croda, Inc.); and SA9OHCO, which is $C_{18}H_{37}CH_2$ $(CON(CH_3))$—$CH_2$ $(CHOH)_4$ $(CH_2OH)_2$ (manufactured by Eastman Kodak Co.); decanoyl-N-methylglucamide; n-decyl-β-D-glucopyranoside; n-decyl-β-D-maltopyranoside; n-dodecyl-β-D-glucopyranoside; n-dodecyl-β-D-maltoside; heptanoyl-N-methylglucamide; n-heptyl-β-D-glucopyranoside; n-heptyl-β-D-thioglucoside; n-hexyl-β-D-glucopyranoside; nonanoyl-N-methylglucamide; n-nonyl-β-D-glucopyranoside; octanoyl-N-methylglucamide; n-octyl-β-D-glucopyranoside; octyl-β-D-thioglucopyranoside, methionine (which may be in any of D-form, L-form, and racemic form (DL form)), gum arabic, polyvinylpyrrolidone, and the like. Such dispersants can be used singly or in a combination of two or more.

Most of these dispersants are known pharmaceutical excipients and are described in detail in the Handbook of Pharmaceutical Excipients, published jointly by the American Pharmaceutical Association and the Pharmaceutical Society of Great Britain (The Pharmaceutical Press, 1986). Pharmaceutical excipients described in this publication can also be used. Commercially available dispersants may be used, or dispersants can be prepared by using techniques known in the art.

The concentration of the dispersant in the injectable preparation is preferably about 0.1 to 45 mg/mL, more preferably about 0.5 to 40 mg/mL, and even more preferably about 0.6 to 35 mg/mL, based on the total volume of the injectable preparation. The proportion of the dispersant in the injectable preparation is preferably about 0.01 to 10 wt %, more preferably about 0.05 to 8 wt %, and even more preferably about 0.06 to 5 wt %. The amount of the dispersant is preferably about 0.01 to 45 parts by weight, more preferably about 0.1 to 40 parts by weight, and even more preferably about 0.5 to 35 parts by weight, based on 100 parts by weight of Compound (I) or a salt thereof.

Dispersants may also have functions as other additives. In this case, the concentration, proportion, and amount of dispersant are the total of the concentrations, proportions, and amounts of such additives used.

Examples of isotonizing agents include non-electrolytic osmotic modulating agents, such as mannitol, sucrose, maltose, xylitol, glucose, starch, sorbitol, glycerol, and propylene glycol; and electrolytic osmotic modulating agents, such as sodium chloride, potassium chloride, sodium sulfate, and magnesium chloride. Such isotonizing agents can be used singly or in a combination of two or more.

When an oily particle binder is used as the particle binder, sorbitol is preferably used. When an aqueous particle binder is used as the binder, sodium chloride is preferably used.

Sugars or sugar alcohols, such as mannitol, trehalose, sucrose, maltose, xylitol, and sorbitol, are preferable because they can be expected to stabilize the produced injectable preparation during frozen storage.

The concentration of the isotonizing agent in the injectable preparation is preferably about 0.1 to 70 mg/mL, more preferably about 0.5 to 60 mg/mL, and even more preferably about 1 to 55 mg/mL. The proportion of the isotonizing agent in the injectable preparation is preferably about 0.05 to 10 wt %, more preferably about 0.1 to 7 wt %, and even more preferably about 0.2 to 5 wt %. The amount of the isotonizing agent is preferably about 1 to 70 parts by weight, more preferably about 2 to 60 parts by weight, and even more preferably about 4 to 55 parts by weight, based on 100 parts by weight of Compound (I) or a salt thereof.

Isotonizing agents may also have functions as other additives. In this case, the concentration, proportion, and amount of isotonizing agent are the total of the concentrations, proportions, and amounts of such additives used.

Examples of stabilizers include ascorbic acid, ascorbic acid derivatives (such as erythorbic acid, and sodium ascorbate), methionine, and the like. The methionine may be in any of D form, L form, and racemic form (DL form).

The concentration of the stabilizer in the injectable preparation is preferably about 0.1 to 5 mg/mL, more preferably about 0.5 to 4 mg/mL, and even more preferably about 1 to 3 mg/mL. The proportion of the stabilizer in the injectable preparation is preferably about 0.01 to 5 wt %, more preferably about 0.05 to 2 wt %, and even more preferably about 0.1 to 0.5 wt %. The amount of the stabilizer is preferably about 0.1 to 5 parts by weight, more preferably about 0.5 to 4 parts by weight, and even more preferably about 0.1 to 3 parts by weight, based on 100 parts by weight of Compound (I) or a salt thereof.

Stabilizers may also have functions as other additives. In this case, the concentration, proportion, and amount of stabilizer are the total of the concentrations, proportions, and amounts of such additives used.

Examples of buffers include sodium phosphate, potassium phosphate, tris buffers, sodium hydrogenphosphate, sodium dihydrogenphosphate, trisodium phosphate, and hydrates thereof. Specific examples of hydrates include sodium dihydrogenphosphate dihydrate and disodium hydrogenphosphate dodecahydrate. Such buffers may be used singly or in a combination of two or more.

The proportion and amount of the buffer are such that the injectable preparation containing Compound (I) or a salt thereof can be adjusted to a pH described below (preferably a pH of about 4 to 9, more preferably about 4.5 to 8.5, and even more preferably about 5 to 8). Generally, the proportion of the buffer in the injectable preparation may suitably change according to the type of buffer, etc. For example, it is preferably about 0.01 to 10 mg/mL, more preferably about 0.1 to 7 mg/mL, and even more preferably about 0.2 to 5 mg/mL, based on the total weight of the injectable preparation. The concentration of the buffer in the injectable preparation is preferably about 0.001 to 5 wt %, more preferably about 0.01 to 1 wt %, and even more preferably about 0.02 to 0.8 wt %. The amount of the buffer in the injectable preparation may also suitably change according to the type of buffer, etc. For example, the amount of the buffer is preferably about 0.01 to 10 parts by weight, more preferably about 0.1 to 5 parts by weight, and even more preferably about 0.2 to 3 parts by weight, based on 100 parts by weight of Compound (I) or a salt thereof.

When the injectable preparation has a high pH and is adjusted to a lower pH, an acidic pH adjuster, such as hydrochloric acid, acetic acid, or citric acid, can be used.

When the injectable preparation has a low pH and is adjusted to a higher pH, a basic pH adjuster, such as sodium hydroxide, potassium hydroxide, calcium carbonate, magnesium oxide, or magnesium hydroxide, can be used. Sodium hydroxide is preferably used.

Such pH adjusters may be used singly or in a combination of two or more.

The proportion and amount of the pH adjuster are such that the injectable preparation containing Compound (I) or a salt thereof can be adjusted to a pH described below (preferably a pH of about 4 to 9, more preferably about 4.5 to 8.5, and even more preferably about 5 to 8). To achieve the desired pH, an acid or a base is suitably selected.

A suspension is obtained by suspending Compound (I) or a salt thereof, and a vehicle for Compound (I) or a salt thereof in water for injection. Although there is no particular limitation, it is preferable that the vehicle is dissolved in water for injection to prepare an injectable solution and Compound (I) or a salt thereof is suspended in the injectable solution.

Sterilized water (pure water) is used as the water for injection. The amount of water for injection is preferably about 0.7 to 1.0 mL, and more preferably about 0.8 to 0.9 mL per mL of the injectable preparation.

According to the injectable preparation of the present invention, the suspension as is can be used as an injectable preparation.

The obtained injectable preparation preferably has a pH of about 4 to 9, more preferably about 4.5 to 8.5, and even more preferably about 5 to 8. When the pH is set to about 5 or more, a stable suspension in which a smaller amount of a drug is dissolved in an injection solvent can be preferably prepared. When the pH is set to about 8 or less, a stable suspension by which stimulation is reduced can be preferably prepared.

Compound (I) or a salt thereof, and a vehicle for Compound (I) or a salt thereof used in the injectable preparation of the present invention may be a freeze-dried product or a powder mixture. Such a freeze-dried product can be obtained, for example, by suspending Compound (I) or a salt thereof and a vehicle for Compound (I) or a salt thereof in water, and then freeze-drying the suspension. The proportions of Compound (I) or a salt thereof, and a vehicle for Compound (I) or a salt thereof in the freeze-dried product or powder mixture can be suitably set to the above proportions by subsequent addition of water for injection.

The freeze-dried product or powder mixture may also be formulated into an injectable preparation by the addition of water for injection at the time of use.

The method for producing the injectable preparation of the present invention is not particularly limited. For example, when an aqueous particle binder is used as the particle binder, the injectable preparation can be produced by using a process comprising the steps of dissolving a vehicle in water for injection to prepare an injectable solution and further suspending Compound (I) or a salt thereof in the obtained injectable solution.

When an oily particle binder is used as the particle binder, the injectable preparation can be produced, for example, by using a process comprising the steps of dissolving a vehicle in water for injection and adding an oily particle binder filtered through a sterilized oleophilic filter to obtain an injectable solution, further incorporating Compound (I) or a salt thereof in the obtained injectable solution, and stirring and heating the resulting mixture.

The injectable preparation containing Compound (I) or a salt thereof according to the present invention almost creates no patient compliance problems and can be preferably administered to deliver a drug.

When the injectable preparation containing Compound (I) or a salt thereof according to the present invention is produced, it is particularly preferable that all production steps are sterile. That is, it is preferable that a sterile Compound (I) or a salt thereof, and a sterile vehicle are mixed aseptically to form a sterile suspension.

The method for obtaining a sterile bulk powder of Compound (I) or a salt thereof includes, for example, the following methods: sterilization by means of ionizing irradiation with an electron beam or gamma rays, aseptic crystallization, UV irradiation, autoclaving, etc.; gas sterilization with ethylene oxide or hydrogen peroxide; suspended particle filter sterilization; and an aseptic technique within a clean bench.

Vehicles (a particle binder, a dispersant (suspending agent), an isotonizing agent, a stabilizer, a buffer, a pH adjuster, a solvent) and water are preferably sterilized by autoclaving, filtration, etc. after being prepared.

The preparation comprising Compound (I) or a salt thereof according to the present invention can be preferably used to treat schizophrenia and associated disorders (such as bipolar disorder and dementia) in human patients. A preferable dose of the injectable preparation of the present invention is, for example, a single injection or multiple injections of the preparation containing Compound (I) or a salt thereof in a concentration of about 50 to 150 mg per mL of the preparation, which can be given once a month. Although the injectable preparation is preferably administered intramuscularly, subcutaneous injection is also acceptable.

Because the sustained release period during which Compound (I) or a salt thereof is released into the body is long, the injectable preparation of the present invention is useful as a depot medication (a sustained-release injectable preparation). Furthermore, the injectable preparation of the present invention is less irritating and is also excellent in terms of stability. Because poor syringability results in increased irritation, good syringability is preferable.

According to the injectable preparation of the present invention, a therapeutic amount of the above sustained-release injectable preparation can be administered to a patient in need of treatment and can treat central nervous system diseases.

Specific examples of the central nervous system diseases treated by the injectable preparation of the present invention that contains a dihydrate of benzothiophene compound include schizophrenia, such as treatment-resistant, refractory and chronic schizophrenia, emotional disturbance, psychotic disorder, mood disorder, bipolar disorder (e.g., bipolar I disorder and bipolar II disorder), mania, depression, endogenous depression, major depression, melancholic and treatment-resistant depression, dysthymic disorder, cyclothymic disorder, anxiety disorder (e.g., panic attack, panic disorder, agoraphobia, social phobia, obsessive-compulsive disorder, post traumatic stress disorder, generalized anxiety disorder, and acute stress disorder), somatoform disorder (e.g., hysteria, somatization disorder, conversion disorder, pain disorder, and hypochondria), factitious disorder, dissociative disorder, sexual disorder (e.g., sexual dysfunction, libido disorder, sexual arousal disorder, and erectile dysfunction), eating disorder (e.g., anorexia nervosa and bulimia nervosa), sleep disorder, adjustment disorder, substance-related disorder (e.g., alcohol abuse, alcohol intoxication and drug addiction, amphetamine addiction, and narcotism), anhedonia (e.g., iatrogenic anhedonia, anhedonia of a psychic or mental cause, anhedonia associated with depression, anhedonia associated with schizophrenia), delirium, cognitive impairment, cognitive impairment associated with Alzheimer's disease, Parkinson's disease, and other neurodegenerative diseases, BPSD (Behavioral and Psychological Symptoms of Dementia) caused by cognitive impairment, cognitive impairment in schizophrenia, cognitive impairment caused by treatment-resistant, refractory or chronic schizophrenia, vomiting, motion sickness, obesity, migraine, pain, mental retardation, autistic disorder (autism), Tourette's syndrome, tic disorder, attention deficit hyperactivity disorder, conduct disorder, Down's syndrome, etc.; and various other central nervous system diseases. The pharmaceutical preparation of the present invention is extremely effective for the amelioration of these central nervous system diseases. In particular, the pharmaceutical preparation of the present invention is effective for the treatment or prevention of the recurrence of schizophrenia, bipolar disorder or depression.

One example of the particularly preferable particle binder of the injectable preparation of the present invention comprises (i) sodium chloride, and (ii) at least one member selected from the group consisting of polyoxyethylene sorbitan fatty acid esters, block copolymers of ethylene oxide and propylene oxide, and polyethylene glycol. Here, component (ii) is preferable at least one member selected from the group consisting of polyoxyethylene sorbitan fatty acid esters and polyethylene glycol. In particular, in the injectable preparation using a dihydrate of Compound (I), use of the particle binder is preferable.

By containing Compound (I) or a salt thereof or Compound (I) or a salt thereof and sodium chloride, Compound (I) or a salt thereof can desirably form secondary particles; however, syringability is not excellent. Compound (ii) described above improves the syringability; therefore, (i) sodium chloride and component (ii) are preferably used in combination as a particle binder.

As described above, the injectable preparation of the present invention is such that the secondary particles of Compound (I) or a salt thereof precipitate when stood for a long period of time but the precipitate does not solidify; upon a simple operation such as gentle stirring or slightly shaking with the hand, the secondary particles are easily suspended and revert to a suspension. Therefore, a prefilled syringe into which the injectable preparation of the present invention is filled beforehand is useful, in particular, in clinical practice. In other words, a syringe that is prefilled with the injectable preparation has excellent storage stability and is simple and convenient since even when precipitation occurs due to the prefilled syringe having stood for some time, it easily returns to a suspension by shaking with hand, etc. The scope of the present invention encompasses such a prefilled syringe and a kit comprising the prefilled syringe.

Effect of the Invention

The present invention provides a long-acting medication administration form of Compound (I) or a salt thereof, which is usable as a sustained release injectable preparation that releases a therapeutically effective amount of Compound (I) or a salt thereof over a period of at least one week. The injectable preparation of the present invention exhibits superior sustained release properties after administration compared to an injectable preparation that contains Compound (I) or a salt thereof in the form of primary particles. (More specifically, excessive increase in blood concentration is not observed and the sustainability of the medicinal efficacy is equal or better). Furthermore, even when the secondary particles of Compound (I) or a salt thereof have precipitated after being allowed to stand for a long period of time, the precipitate does not solidify, and it easily returns to a suspension as the secondary particles are easily suspended by a simple operation such as gentle stirring or shaking with hand. Therefore, the injectable preparation of the present invention can be easily restored to a suspension from the precipitate that is formed after long-term storage (i.e., for five days or more), and the restored suspension as is can be preferably injected into a patient.

MODE FOR CARRYING OUT THE INVENTION

EXAMPLES

Figure 1:
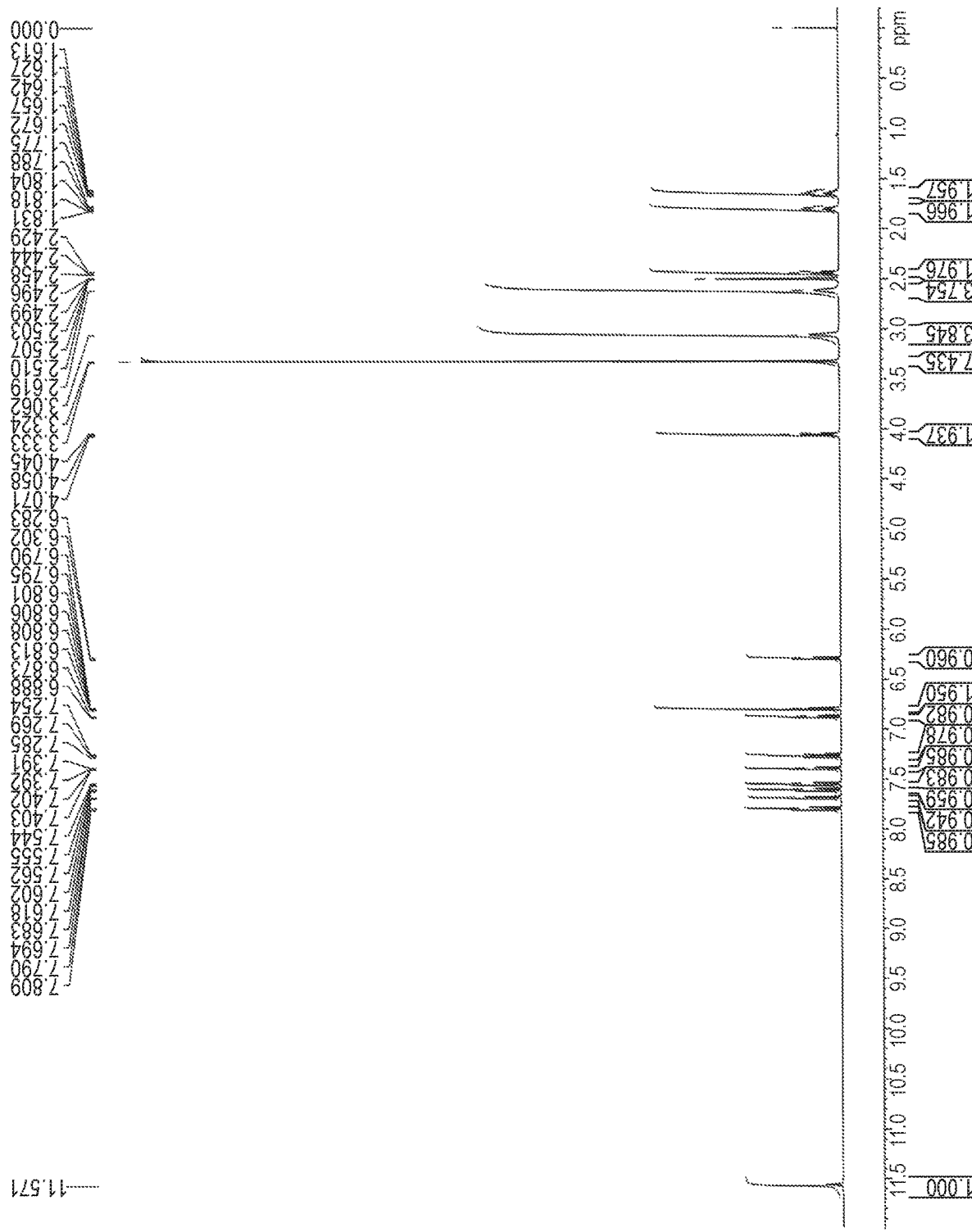
FIG. 1 shows the $^1$H-NMR spectrum of the benzothiophene compound represented by Formula (I) synthesized in Production Example 1.

The present invention is described in further detail with reference to Examples and Test Examples. However, the scope of the invention is not limited to these Examples.

Production Example 1: Synthesis of Dihydrate of Compound (I)

Methanol (149 L), 7-hydroxy-1H-quinolin-2-one (14.87 kg), and potassium hydroxide (6.21 kg) were mixed in a reaction vessel, and the resulting mixture was stirred. After dissolution, 1-bromo-4-chlorobutane (47.46 kg) was added thereto, and the resulting mixture was stirred under reflux for seven hours. Thereafter, the mixture was stirred at 10° C. for one hour. The precipitated crystal was centrifuged and washed with methanol (15 L). The wet crystal was collected and placed in a tank. Water (149 L) was added thereto, followed by stirring at room temperature. After centrifugation, the result was washed with water (30 L). The wet crystal was collected and placed in a tank. After adding methanol (74 L), the mixture was stirred under reflux for one hour, cooled to 10° C., and then stirred. The precipitated crystal was centrifuged and washed with methanol (15 L). The separated crystal was dried at 60° C. to obtain 7-(4-chlorobutoxy)-1H-quinolin-2-one (15.07 kg).

Thereafter, water (20 L), potassium carbonate (1.84 kg), 1-benzo[b]thiophen-4-yl-piperazine hydrochloride (3.12 kg), and ethanol (8 L) were mixed in a reaction vessel, and then stirred at 50° C. 7-(4-Chlorobutoxy)-1H-quinolin-2-one (2.80 kg) was added to the mixture, and stirred under reflux for nine hours. After concentrating the solvent to 8 L under ordinary pressure, the mixture was stirred at 90° C. for one hour, and then cooled to 9° C. The precipitated crystal was centrifuged, and then sequentially washed with water (8 L) and ethanol (6 L). The separated crystal was dried at 60° C. to obtain a crude product. The crude product (4.82 kg) and ethanol (96 L) were mixed in a reaction vessel, and acetic acid (4.8 L) was introduced into the reaction vessel. The mixture was stirred under reflux for one hour to dissolve the crude product. After introducing hydrochloric acid (1.29 kg), the mixture was cooled to 10° C. The mixture was heated again, refluxed for one hour, and cooled to 7° C. The precipitated crystal was centrifuged and washed with ethanol (4.8 L). The separated crystal was dried at 60° C. to obtain 7-[4-(4-benzo[b]thiophen-4-yl-piperazin-1-yl)butoxy]-1H-quinolin-2-one hydrochloride (5.09 kg). The resulting 7-[4-(4-benzo[b]thiophen-4-yl-piperazin-1-yl)butoxy]-1H-quinolin-2-one hydrochloride (5.00 kg), ethanol (45 L), and water (30 L) were mixed in a reaction vessel. The mixture was stirred under reflux to dissolve the 7-[4-(4-benzo[b]thiophen-4-yl-piperazin-1-yl)butoxy]-1H-quinolin-2-one hydrochloride. Activated carbon (500 g) and water (5 L) were added thereto, and an activated carbon treatment was conducted under reflux for 30 minutes. After performing hot filtration, a solution containing sodium hydroxide (511 g) dissolved in water (1.5 L) was flowed into the reaction vessel while stirring the filtrate under reflux. After stirring under reflux for 30 minutes, water (10 L) was introduced thereto, and the mixture was cooled to approximately 40° C. The precipitated crystal was centrifuged and washed with water (125 L). The separated crystal was dried at 80° C. to obtain 7-[4-(4-benzo[b]thiophen-4-yl-piperazin-1-yl)butoxy]-1H-quinolin-2-one (3.76 kg).

The 7-[4-(4-benzo[b]thiophen-4-yl-piperazin-1-yl)butoxy]-1H-quinolin-2-one (3.2 kg) obtained above, ethanol (64 L), water (74 L), and acetic acid (1.77 kg) were mixed in a reaction vessel to prepare an acid liquid mixture. The liquid mixture was stirred under reflux to dissolve the 7-[4-(4-benzo[b]thiophen-4-yl-piperazin-1-yl)butoxy]-1H-quinolin-2-one (reflux temperature: 84° C.). After cooling to −5° C., the solution obtained above was introduced, over a period of 30 minutes, into a solution containing 25% sodium hydroxide (5.9 kg) and water (54 L) that was cooled to 0° C., to prepare a liquid mixture with pH10. After stirring at 5° C. or below for one hour, the mixture was heated to 20 to 30° C. and further stirred for seven hours to conduct solid-liquid separation. Washing with water (320 L) was performed until alkali in the solid component disappeared (i.e., until the pH value of the filtrate became 7). The solid component was then air-dried until its weight became constant (i.e., until there was no longer any change of weight observed) to obtain a white solid 7-[4-(4-benzo[b]thiophen-4-yl-piperazin-1-yl)butoxy]-1H-quinolin-2-one dihydrate (unground, 3.21 kg).

FIG. 1 shows the $^1$H-NMR spectrum (DMSO-$d_6$, TMS) of the dihydrate synthesized by the aforesaid method. As shown in FIG. 1, in the $^1$H-NMR spectrum (DMSO-$d_6$, TMS), peaks were observed at 1.64 ppm (tt, J=7.4 Hz, J=7.4 Hz, 2H), 1.80 ppm (tt, J=7.0 Hz, J=7.0 Hz, 2H), 2.44 ppm (t, J=7.5 Hz, 2H), 2.62 ppm (br, 4H), 3.06 ppm (br, 4H), 3.32 ppm (s, 4H+H$_2$O), 4.06 ppm (t, J=6.5 Hz, 2H), 6.29 ppm (d, J=9.5 Hz, 1H), 6.80 ppm (d, J=2.5 Hz, 1H), 6.80 ppm (dd, J=2.5 Hz, J=9.0 Hz, 1H), 6.88 ppm (d, J=7.5 Hz, 1H), 7.27 ppm (dd, J=7.8 Hz, J=7.8 Hz, 1H), 7.40 ppm (dd, J=0.5 Hz, J=5.5 Hz, 1H), 7.55 ppm (d, J=9.0 Hz, 1H), 7.61 ppm (d, J=8.0 Hz, 1H), 7.69 ppm (d, J=5.5 Hz, 1H), 7.80 ppm (d, J=9.5 Hz, 1H), and 11.57 ppm (s, 1H).

Figure 2:
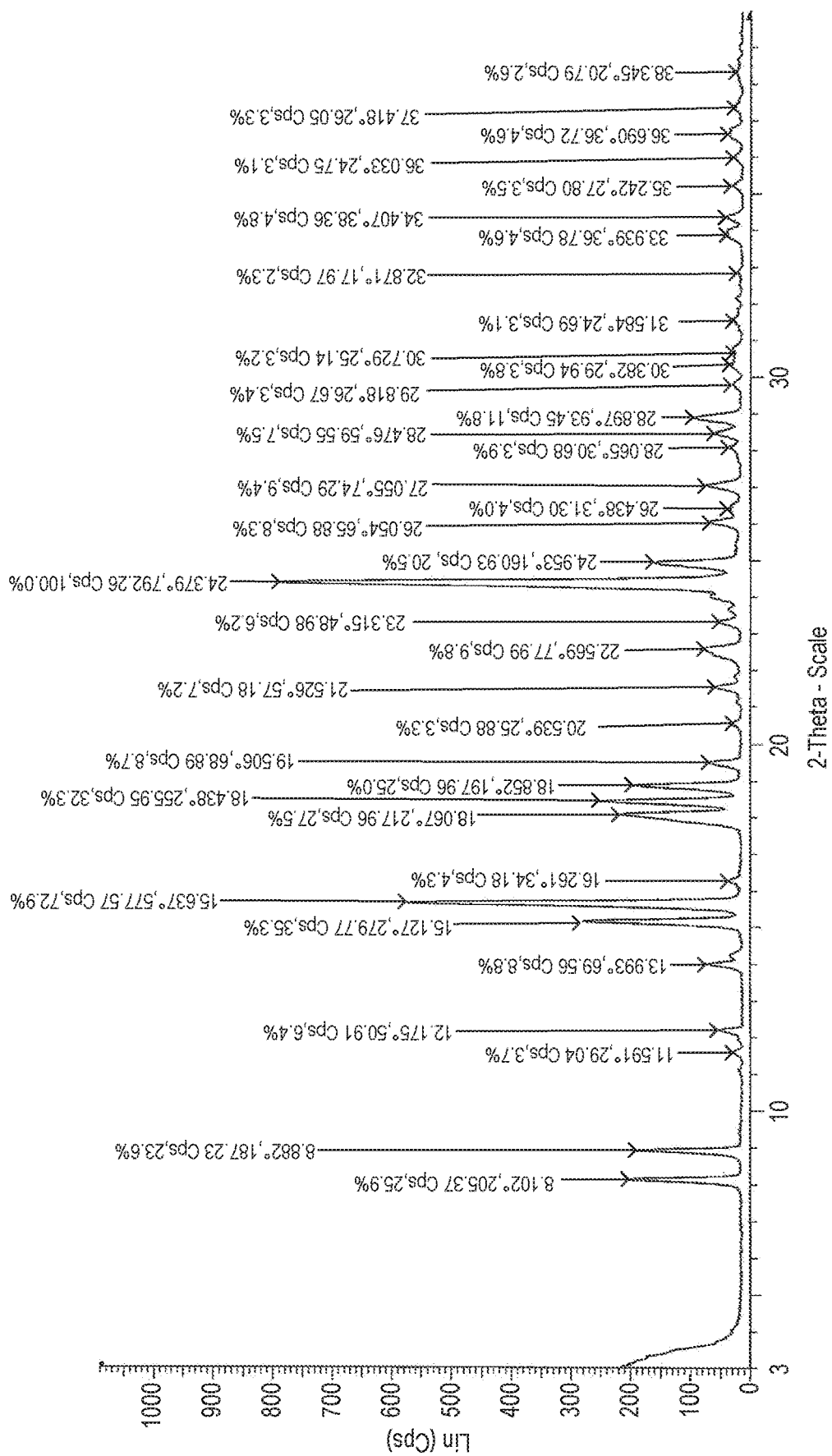
FIG. 2 shows the X-ray powder diffraction pattern of the dihydrate of the benzothiophene compound represented by Formula (I) synthesized in Production Example 1.

The X-ray powder diffraction spectrum of the dihydrate synthesized by the aforesaid method was measured using an X-ray diffractometer (D8 ADVANCE, produced by Bruker AXS). FIG. 2 shows the X-ray powder diffraction spectrum. As shown in FIG. 2, in the X-ray powder diffraction spectrum, diffraction peaks were observed at 2θ=8.1°, 8.9°, 15.1°, 15.6°, and 24.4°. Other than those mentioned above, diffraction peaks were also observed at 2θ=11.6°, 12.2°, 14.0°, 16.3°, 18.1°, 18.4°, 18.9°, 19.5°, 20.5°, 21.5°, 22.6°, 23.3°, 25.0°, 26.1°, 26.4°, 27.1°, 28.1°, 28.5°, 28.9°, 29.8°, 30.4°, 30.7°, 31.6°, 32.9°, 33.9°, 34.4°, 35.2°, 36.0°, 36.7°, 37.4°, and 38.3°.

Figure 3:
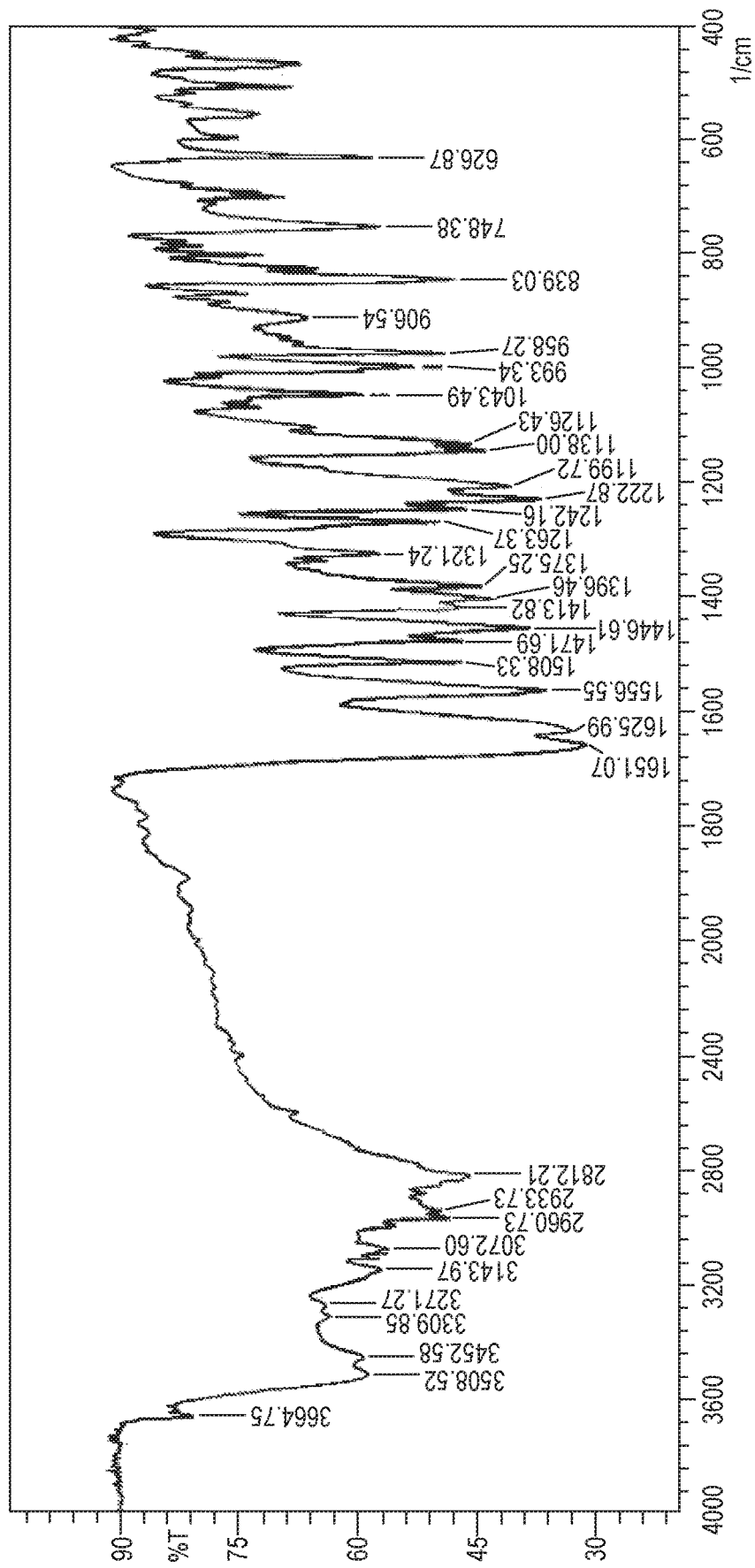
FIG. 3 shows the infrared absorption spectrum of the dihydrate of the benzothiophene compound represented by Formula (I) synthesized in Production Example 1.

The IR (KBr) spectrum of the dihydrate synthesized by the aforesaid method was measured. FIG. 3 shows the IR (KBr) spectrum. As shown in FIG. 3, in the IR (KBr) spectrum, absorption bands were observed in the vicinity of wavenumbers 3509 cm$^{-1}$, 2934 cm$^{-1}$, 2812 cm$^{-1}$, 1651 cm$^{-1}$, 1626 cm$^{-1}$, 1447 cm$^{-1}$, 1223 cm$^{-1}$ and 839 cm$^{-1}$.

Figure 4:
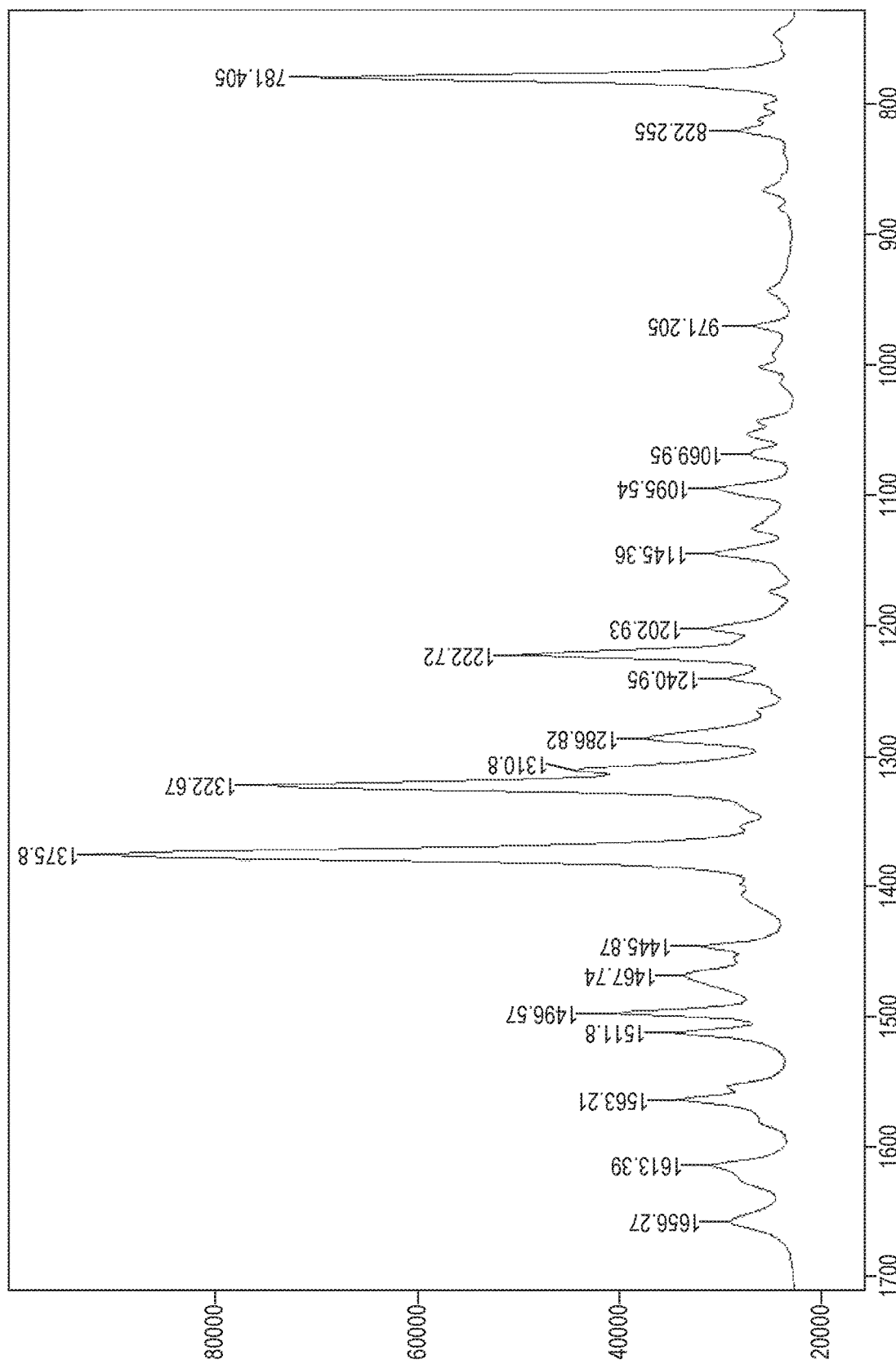
FIG. 4 shows the Raman spectrum of the dihydrate of the benzothiophene compound represented by Formula (I) synthesized in Production Example 1.

The Raman spectrum of the dihydrate synthesized by the aforesaid method was measured. FIG. 4 shows the Raman spectrum. As shown in FIG. 4, in the Raman spectrum, absorption bands were observed in the vicinity of wavenumbers 1497 cm$^{-1}$, 1376 cm$^{-1}$, 1323 cm$^{-1}$, 1311 cm$^{-1}$, 1287 cm$^{-1}$, 1223 cm$^{-1}$, and 781 cm$^{-1}$.

Other than those mentioned above, absorption was also observed in the vicinity of wavenumbers 1656 cm$^{-1}$, 1613 cm$^{-1}$, 1563 cm$^{-1}$, 1512 cm$^{-1}$, 1468 cm$^{-1}$, 1446 cm$^{-1}$, 1241 cm$^{-1}$, 1203 cm$^{-1}$, 1145 cm$^{-1}$, 1096 cm$^{-1}$, 1070 cm$^{-1}$, 971 cm$^{-1}$, and 822 cm$^{-1}$.

Furthermore, the water content of the dihydrate synthesized by the aforesaid method was measured using a moisture meter (CA-100, produced by Mitsubishi Chemical Analytech Co., Ltd.) by the Karl Fischer method. The results showed that the dihydrate had a water content of 7.79% by weight.

Production Example 2: Synthesis of Finely Ground Dihydrate

Dihydrate crystal (2.73 kg) obtained in Production Example 1 was ground using a jet mill. Here, the air pressure was set at 5 kgf/cm$^2$, and the rotational speed of the feeder was set at 20 rpm. As a result, finely ground 7-[4-(4-benzo[b]thiophen-4-yl-piperazin-1-yl)butoxy]-1H-quinolin-2-one dihydrate (2.61 kg, 95.6%) was obtained.

The dihydrate (finely ground product) thus obtained had a mean particle diameter of 5.5 μm. The mean particle diameter was measured using a Microtrack HRA, produced by Nikkiso Co., Ltd.

Figure 5:
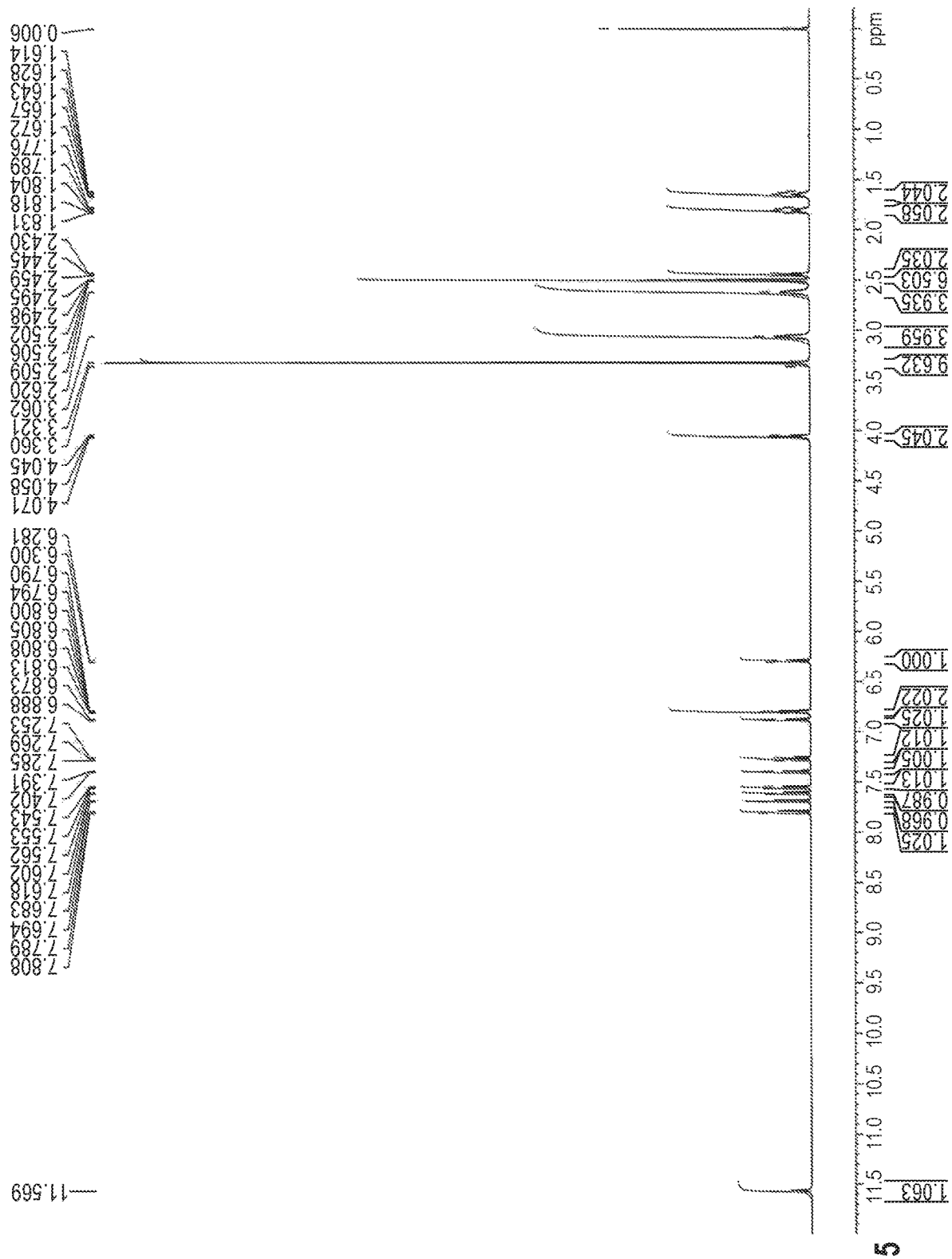
FIG. 5 shows the $^1$H-NMR spectrum of the benzothiophene compound represented by Formula (I) synthesized in Production Example 2.

FIG. 5 shows the $^1$H-NMR spectrum (DMSO-d$_6$, TMS) of the dihydrate synthesized by the above method. As shown in FIG. 5, in the $^1$H-NMR spectrum (DMSO-d$_6$, TMS), peaks were observed at 1.64 ppm (tt, J=7.3 Hz, J=7.3 Hz, 2H), 1.80 ppm (tt, J=6.9 Hz, J=6.9 Hz, 2H), 2.44 ppm (t, J=7.3 Hz, 2H), 2.62 ppm (br, 4H), 3.06 ppm (br, 4H), 3.32 ppm (s, 4H+H$_2$O), 4.06 ppm (t, J=6.5 Hz, 2H), 6.29 ppm (d, J=9.5 Hz, 1H), 6.80 ppm (d, J=2.5 Hz, 1H), 6.80 ppm (dd, J=2.3 Hz, J=9.3 Hz, 1H), 6.88 ppm (d, J=7.5 Hz, 1H), 7.27 ppm (dd, J=8.0 Hz, J=8.0 Hz, 1H), 7.40 ppm (d, J=5.5 Hz, 1H), 7.55 ppm (d, J=9.5 Hz, 1H), 7.61 ppm (d, J=8.0 Hz, 1H), 7.69 ppm (d, J=5.5 Hz, 1H), 7.80 ppm (d, J=9.5 Hz, 1H), and 11.57 ppm (s, 1H).

Figure 6:
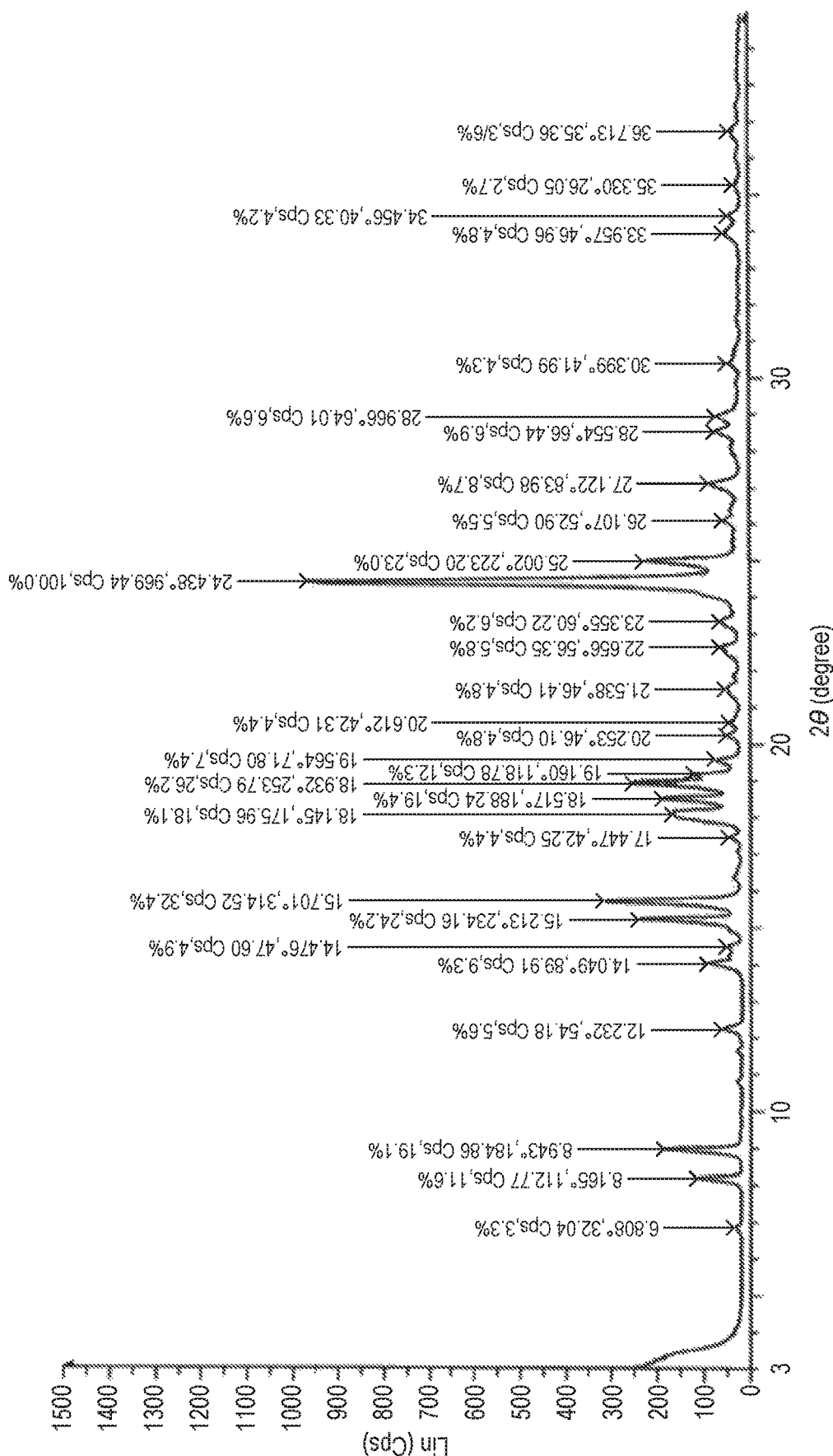
FIG. 6 shows the X-ray powder diffraction pattern of the dihydrate of the benzothiophene compound represented by Formula (I) synthesized in Production Example 2.

The X-ray powder diffraction spectrum of the dihydrate synthesized by the aforesaid method was measured in the same manner as in Production Example 1. FIG. 6 shows the X-ray powder diffraction spectrum. As shown in FIG. 6, in the X-ray powder diffraction spectrum, diffraction peaks were observed at 2θ=8.2°, 8.9°, 15.2°, 15.7°, and 24.4°.

Other than those mentioned above, diffraction peaks were also observed at 2θ=6.8°, 12.2°, 14.0°, 14.5°, 17.4°, 18.1°, 18.5°, 19.0°, 19.2°, 19.6°, 20.3°, 20.6°, 21.5°, 22.7°, 23.4°, 25.0°, 26.1°, 27.1°, 28.6°, 29.0°, 30.4°, 34.0°, 34.5°, 35.3°, and 36.7°.

Figure 7:
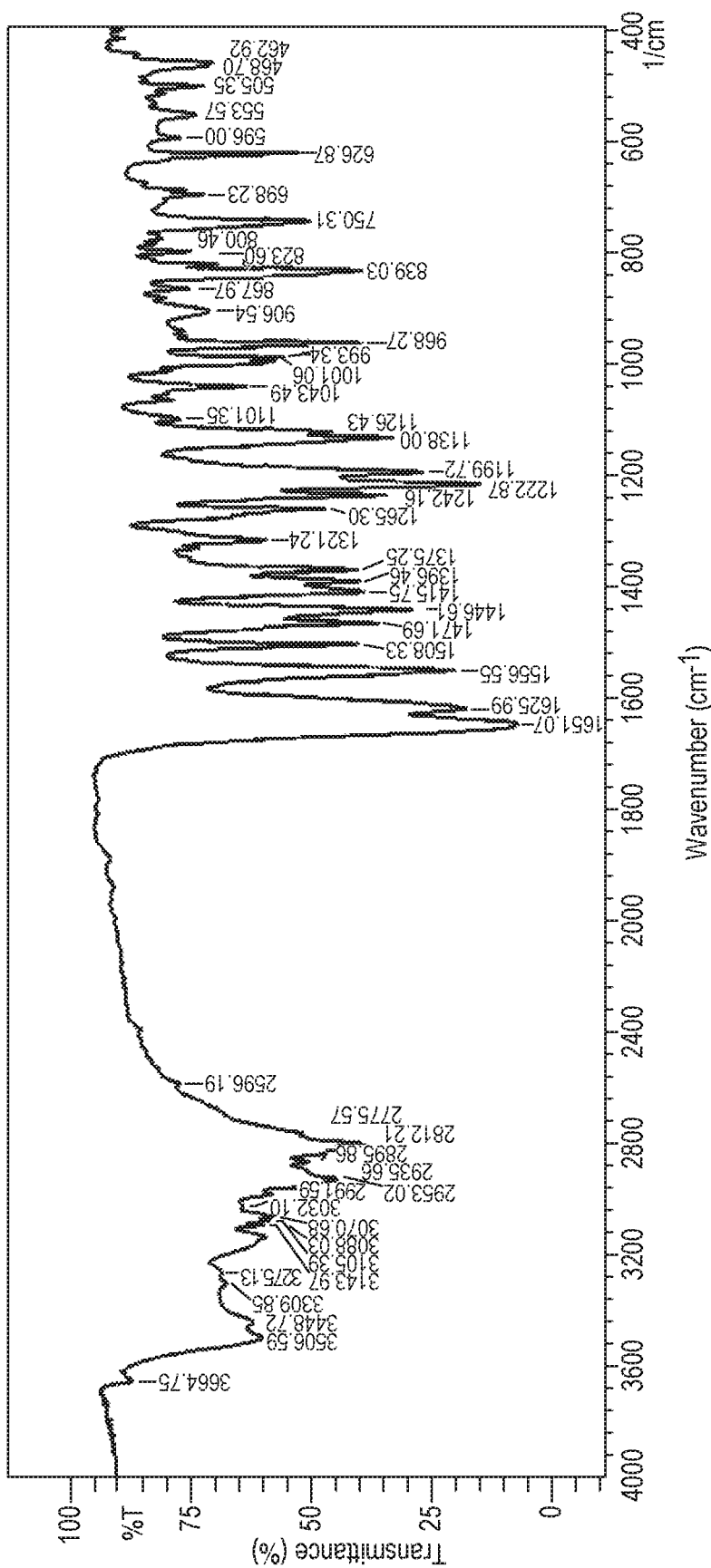
FIG. 7 shows the infrared absorption spectrum of the dihydrate of the benzothiophene compound represented by Formula (I) synthesized in Production Example 2.

The IR (KBr) spectrum of the dihydrate synthesized by the aforesaid method was measured in the same manner as in Production Example 1. FIG. 7 shows the IR (KBr) spectrum. As shown in FIG. 7, in the IR (KBr) spectrum, absorption bands were observed in the vicinity of wavenumbers 3507 cm$^{-1}$, 2936 cm$^{-1}$, 2812 cm$^{-1}$, 1651 cm$^{-1}$, 1626 cm$^{-1}$, 1447 cm$^{-1}$, 1223 cm$^{-1}$, and 839 cm$^{-1}$.

Figure 8:
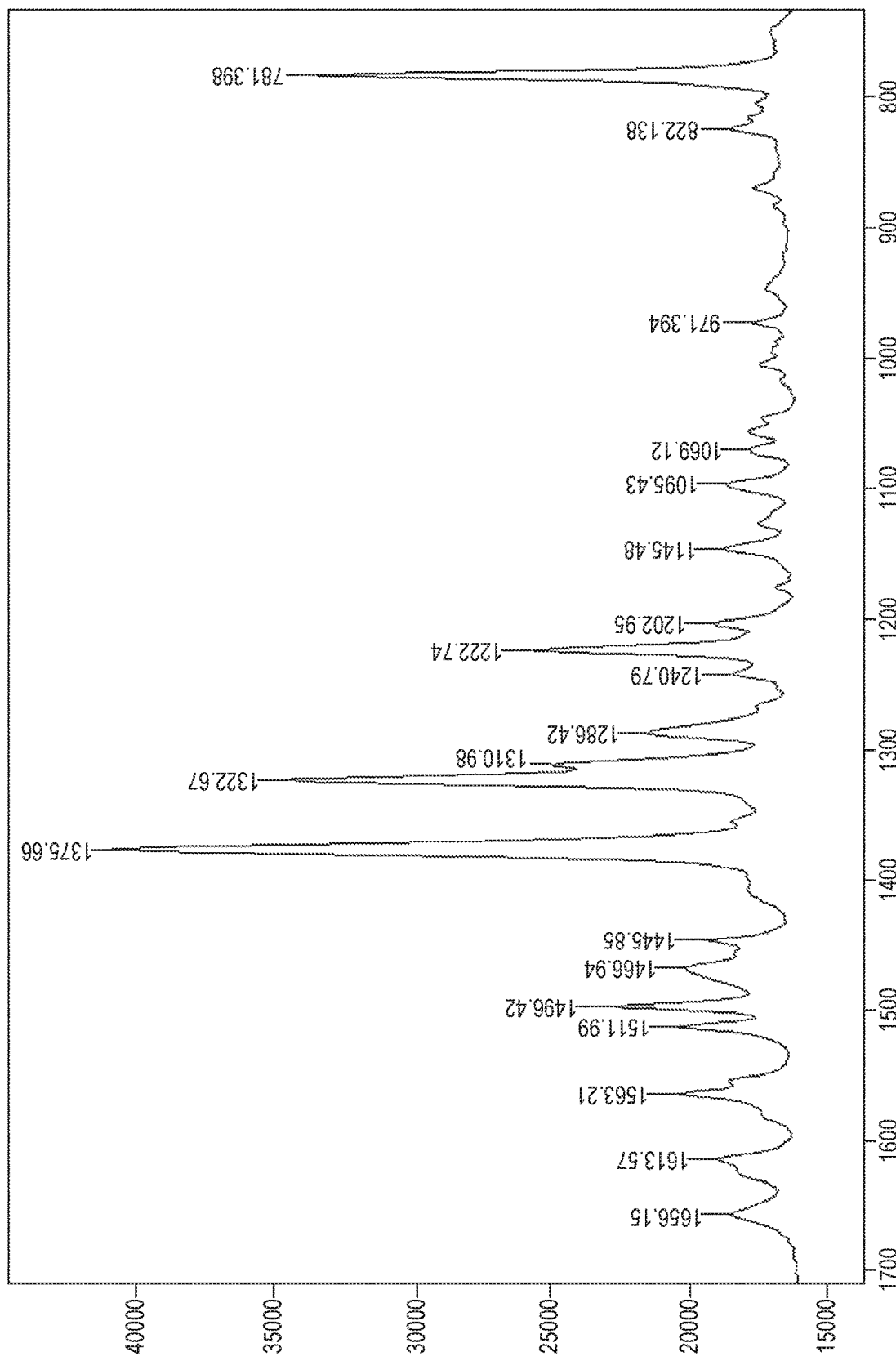
FIG. 8 shows the Raman spectrum of the dihydrate of the benzothiophene compound represented by Formula (I) synthesized in Production Example 2.

The Raman spectrum of the dihydrate synthesized by the aforesaid method was measured. FIG. 8 shows the Raman spectrum. As shown in FIG. 8, in the Raman spectrum, absorption bands were observed in the vicinity of wavenumbers 1496 cm$^{-1}$, 1376 cm$^{-1}$, 1323 cm$^{-1}$, 1311 cm$^{-1}$, 1286 cm$^{-1}$, 1223 cm$^{-1}$, and 781 cm$^{-1}$.

Other than those mentioned above, absorption was also observed in the vicinity of wavenumbers 1656 cm$^{-1}$, 1614 cm$^{-1}$, 1563 cm$^{-1}$, 1512 cm$^{-1}$, 1467 cm$^{-1}$, 1446 cm$^{-1}$, 1241 cm$^{-1}$, 1203 cm$^{-1}$, 1145 cm$^{-1}$, 1095 cm$^{-1}$, 1069 cm$^{-1}$, 971 cm$^{-1}$, and 822 cm$^{-1}$.

Furthermore, the water content of the dihydrate synthesized by the aforesaid method was measured using a moisture meter (CA-100, produced by Mitsubishi Chemical Analytech Co., Ltd.) by the Karl Fischer method. The results showed that the dihydrate had a water content of 6.74% by weight.

Production Example 3: Synthesis of 7-[4-(4-benzo[b]thiophen-4-yl-piperazin-1-yl)butoxy]-1H-quinolin-2-one hydrate 7-[4-(4-Benzo[b]thiophen-4-yl-piperazin-1-yl)butoxy]-1H-quinolin-2-one (5.0 kg), ethanol (100 L), water (115 L), and DL-lactic acid (2.29 kg) were mixed to prepare an acid liquid mixture. The liquid mixture was stirred under reflux to dissolve the 7-[4-(4-benzo[b]thiophen-4-yl-piperazin-1-yl)butoxy]-1H-quinolin-2-one (reflux temperature: 82° C.). After cooling to −5° C., the solution obtained above was introduced, over a period of about 15 minutes, into a solution containing sodium hydroxide (1.48 kg) and water (135 L) that was cooled to 1° C., to prepare a liquid mixture with pH11. After being stirred at approximately 2 to 5° C. for three hours, the mixture was heated to 45° C. and further stirred at 45 to 50° C. for two hours to conduct solid-liquid separation. Washing with water (200 L) was performed until alkali in the solid component disappeared (i.e., until the pH value of the filtrate became 7). The solid component was further washed with a liquid mixture of ethanol (15 L) and water (20 L). The solid component was then dried at room temperature until its weight became constant to obtain a white solid 7-[4-(4-benzo[b]thiophen-4-yl-piperazin-1-yl)butoxy]-1H-quinolin-2-one dihydrate (unground, 5.11 kg).

The hydrate thus obtained was the same as that obtained in Production Example 1.

Figure 9:
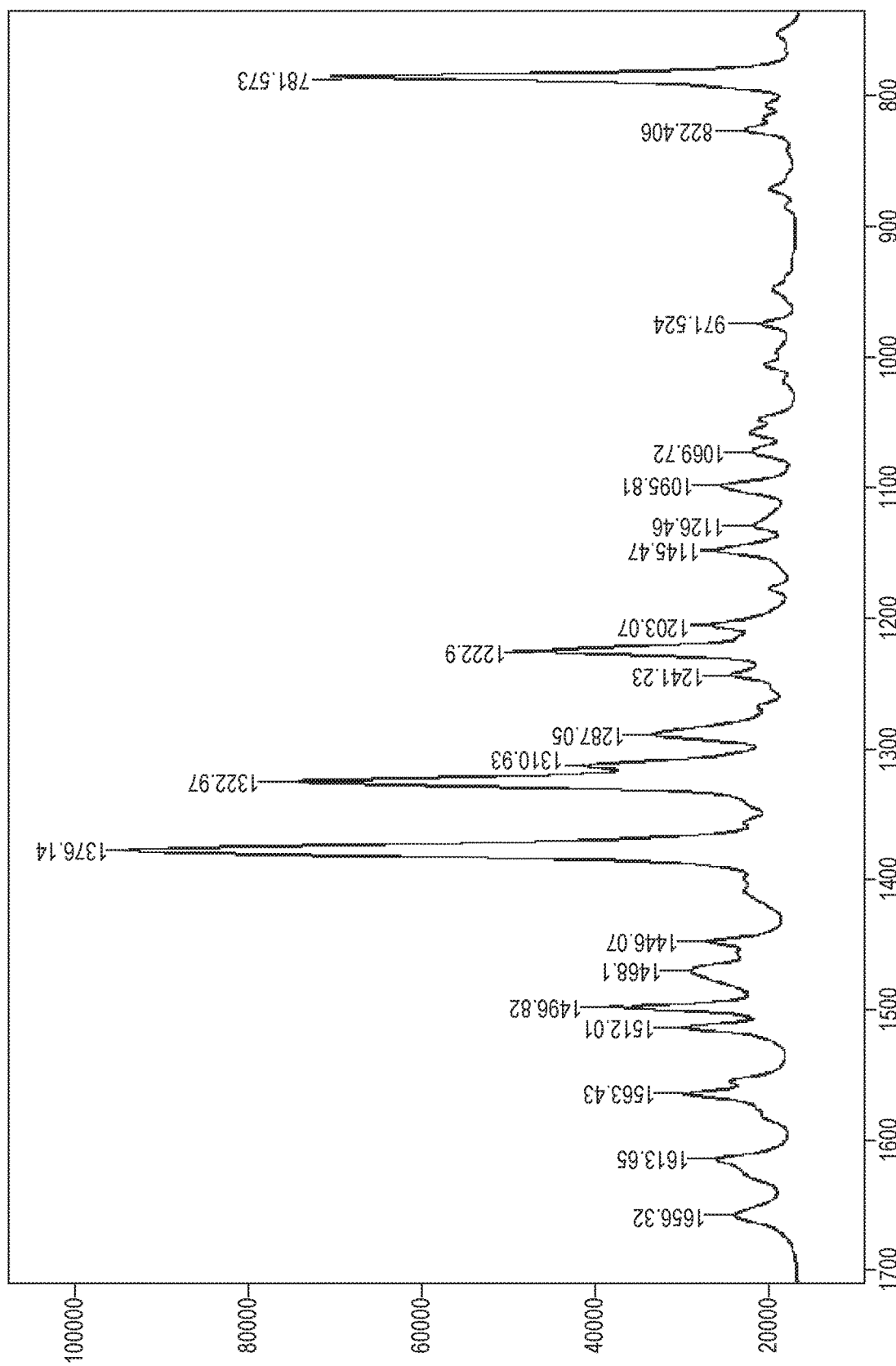
FIG. 9 shows the Raman spectrum of the dihydrate of the benzothiophene compound represented by Formula (I) synthesized in Production Example 3.

The Raman spectrum of the hydrate synthesized by the aforesaid method was measured. FIG. 9 shows the Raman spectrum. As shown in FIG. 9, in the Raman spectrum, absorption bands were observed in the vicinity of wavenumbers 1497 cm$^{-1}$, 1376 cm$^{-1}$, 1323 cm$^{-1}$, 1311 cm$^{-1}$, 1287 cm$^{-1}$, 1223 cm$^{-1}$, and 782 cm$^{-1}$.

Other than those mentioned above, absorption was also observed in the vicinity of wavenumbers 1656 cm$^{-1}$, 1614 cm$^{-1}$, 1563 cm$^{-1}$, 1512 cm$^{-1}$, 1468 cm$^{-1}$, 1446 cm$^{-1}$, 1241 cm$^{-1}$, 1203 cm$^{-1}$, 1145 cm$^{-1}$, 1126 cm$^{-1}$, 1096 cm$^{-1}$, 1070 cm$^{-1}$, 972 cm$^{-1}$, and 822 cm$^{-1}$.

Production Example 4: Synthesis of Anhydride of Compound (I)

The 7-[4-(4-benzo[b]thiophen-4-yl-piperazin-1-yl)butoxy]-1H-quinolin-2-one (700 g) synthesized in Production Example 1, ethanol (14 L), and acetic acid (1.4 L) were mixed in a reaction vessel. The mixture was heated to the reflux temperature (76° C.) to dissolve the 7-[4-(4-benzo[b]thiophen-4-yl-piperazin-1-yl)butoxy]-1H-quinolin-2-one. Concentrated hydrochloric acid (158 mL) was added thereto, and then cooled to 10° C. while being stirred. Thereafter, the mixture was heated again, stirred under reflux for one hour, and then cooled to 10° C. or less. The precipitated solid was filtered by suction and washed with ethanol (0.7 L). The solid component was then air-dried at 60° C. until its weight became constant to obtain a white solid 7-[4-(4-benzo[b]thiophen-4-yl-piperazin-1-yl)butoxy]-1H-quinolin-2-one hydrochloride (814 g). 7-[4-(4-Benzo[b]thiophen-4-yl-piperazin-1-yl)butoxy]-1H-quinolin-2-one hydrochloride (800 g), ethanol (7.2 L), and water (4.8 L) were mixed in a reaction vessel, and the mixture was heated to the reflux temperature (80° C.) while being stirred. After performing hot filtration, the 7-[4-(4-benzo[b]thiophen-4-yl-piperazin-1-yl)butoxy]-1H-quinolin-2-one hydrochloride was dissolved. A solution containing sodium hydroxide (81.6 g) dissolved in water (240 mL) was flowed into the above-obtained solution, and the mixture was stirred under reflux for 30 minutes. Water (2.4 L) was fed to the mixture, followed by cooling to 40° C. while stirring. The precipitated solid was filtered out and washed with water (16 L). The solid was dried at 80° C. to obtain a white solid 7-[4-(4-benzo[b]thiophen-4-yl-piperazin-1-yl)butoxy]-1H-quinolin-2-one anhydride (637 g).

Figure 10:
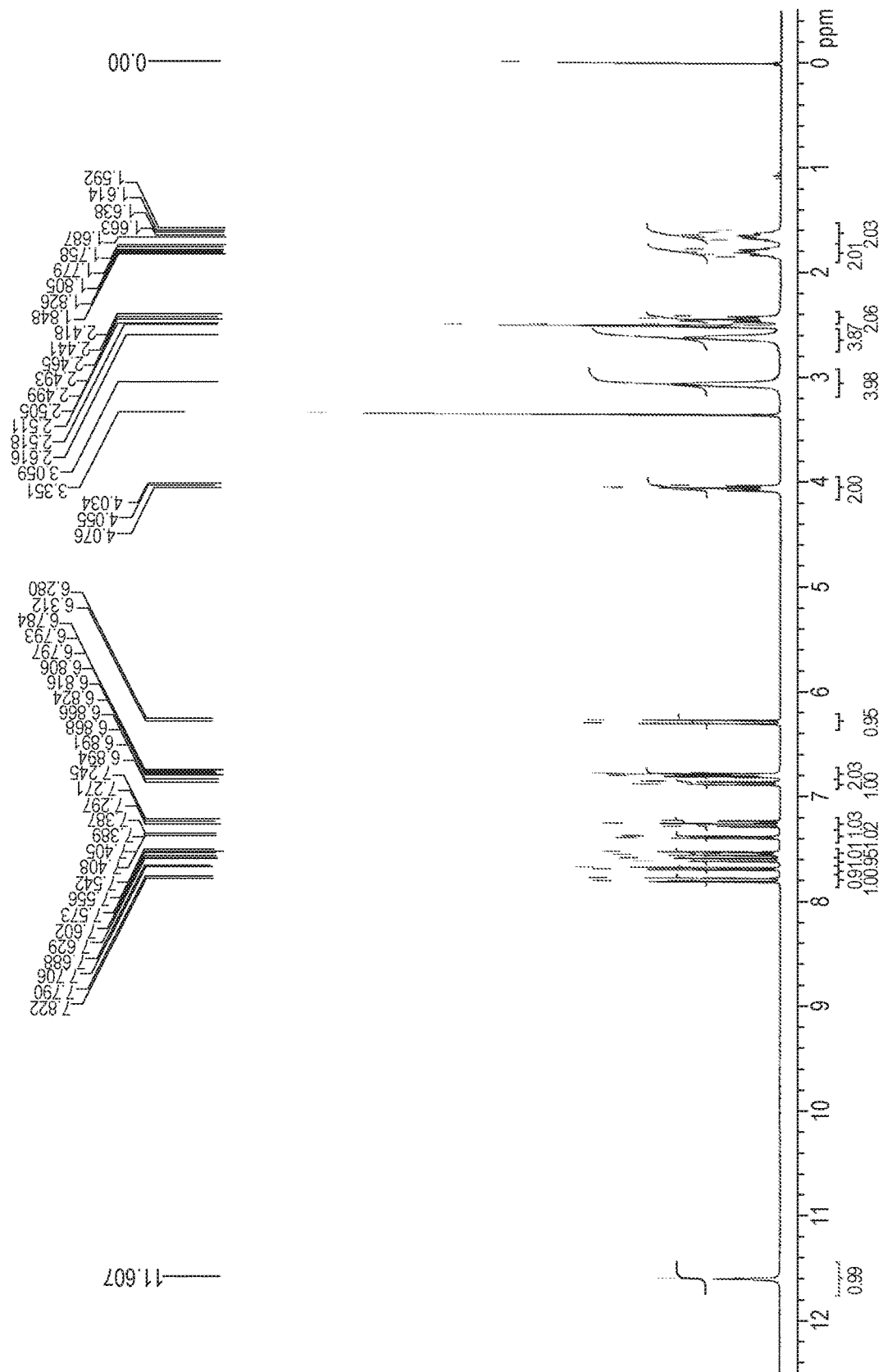
FIG. 10 shows the $^1$H-NMR spectrum of the anhydride of the benzothiophene compound represented by Formula (I) synthesized in Production Example 4.

The $^1$H-NMR spectrum of the anhydride obtained above was measured in the same manner as in Production Example 1. FIG. 10 shows the $^1$H-NMR spectrum (DMSO-$d_6$, TMS). As shown in FIG. 10, in the $^1$H-NMR spectrum (DMSO-$d_6$, TMS), peaks were observed at 1.63 ppm (tt, J=7.3 Hz, J=7.1 Hz, 2H), 1.80 ppm (tt, J=7.3 Hz, J=6.3 Hz, 2H), 2.44 ppm (t, J=7.1 Hz, 2H), 2.61 ppm (m, 4H), 3.05 ppm (m, 4H), 4.05 ppm (t, J=6.3 Hz, 2H), 6.29 ppm (d, J=9.5 Hz, 1H), 6.80 ppm (d, J=2.5 Hz, 1H), 6.80 (dd, J=9.4 Hz, J=2.5 Hz, 1H), 6.88 ppm (dd, J=7.8 Hz, 0.8 Hz, 1H), 7.27 ppm (dd, J=7.8 Hz, J=7.8 Hz, 1H), 7.39 ppm (dd, J=5.6 Hz, 0.8 Hz, 1H), 7.55 ppm (d, J=9.4 Hz, 1H), 7.61 ppm (d, J=7.8 Hz, 1H), 7.69 ppm (d, J=5.6 Hz, 1H), 7.80 ppm (d, J=9.5 Hz, 1H), and 11.60 (s, 1H).

Figure 11:
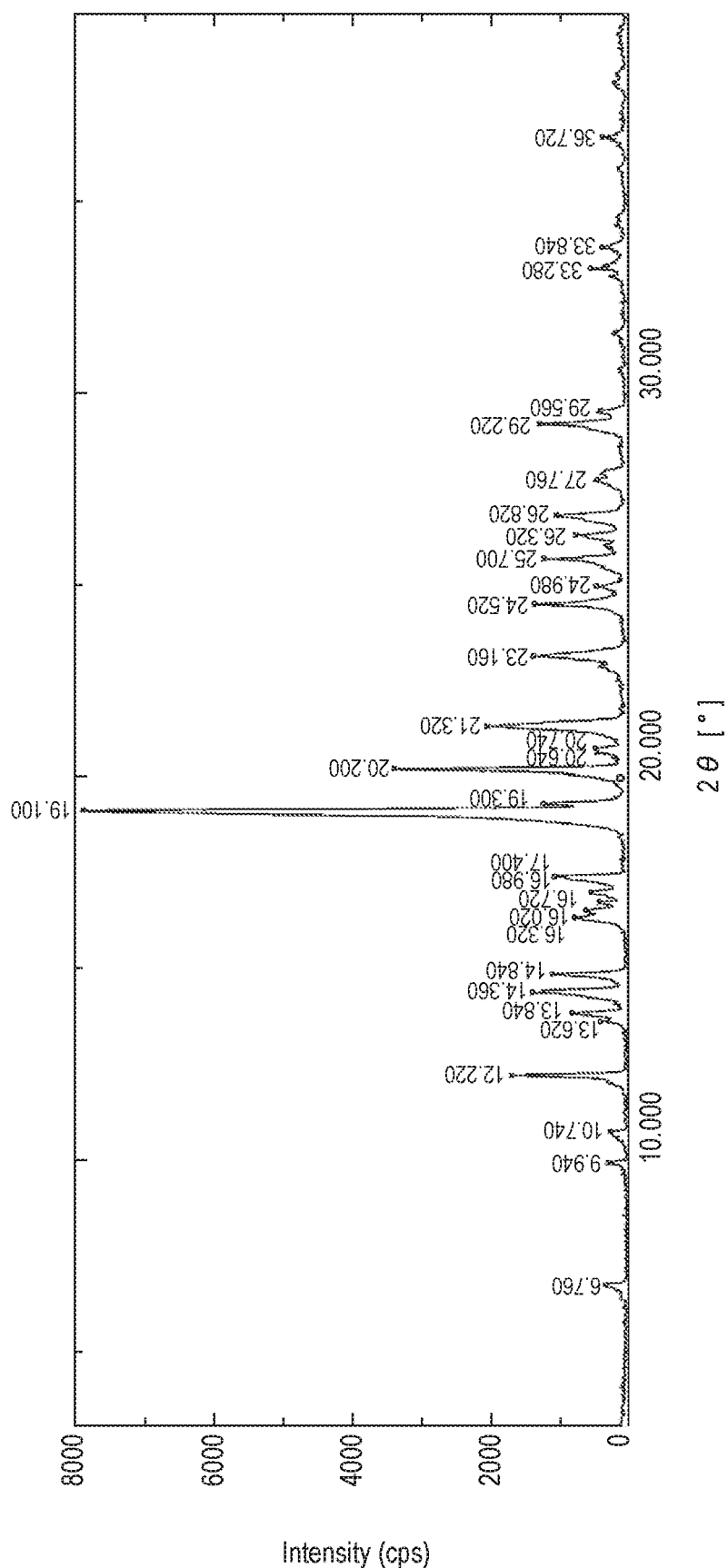
FIG. 11 shows the X-ray powder diffraction pattern of the anhydride of the benzothiophene compound synthesized in Production Example 4.

The X-ray powder diffraction spectrum of the anhydride obtained above was measured in the same manner as in Production Example 1. FIG. 11 shows the X-ray powder diffraction spectrum. As shown in FIG. 11, in the X-ray powder diffraction spectrum, diffraction peaks were observed at 2θ=14.4°, 19.1°, 20.2°, 21.3°, and 23.2°.

Figure 12:
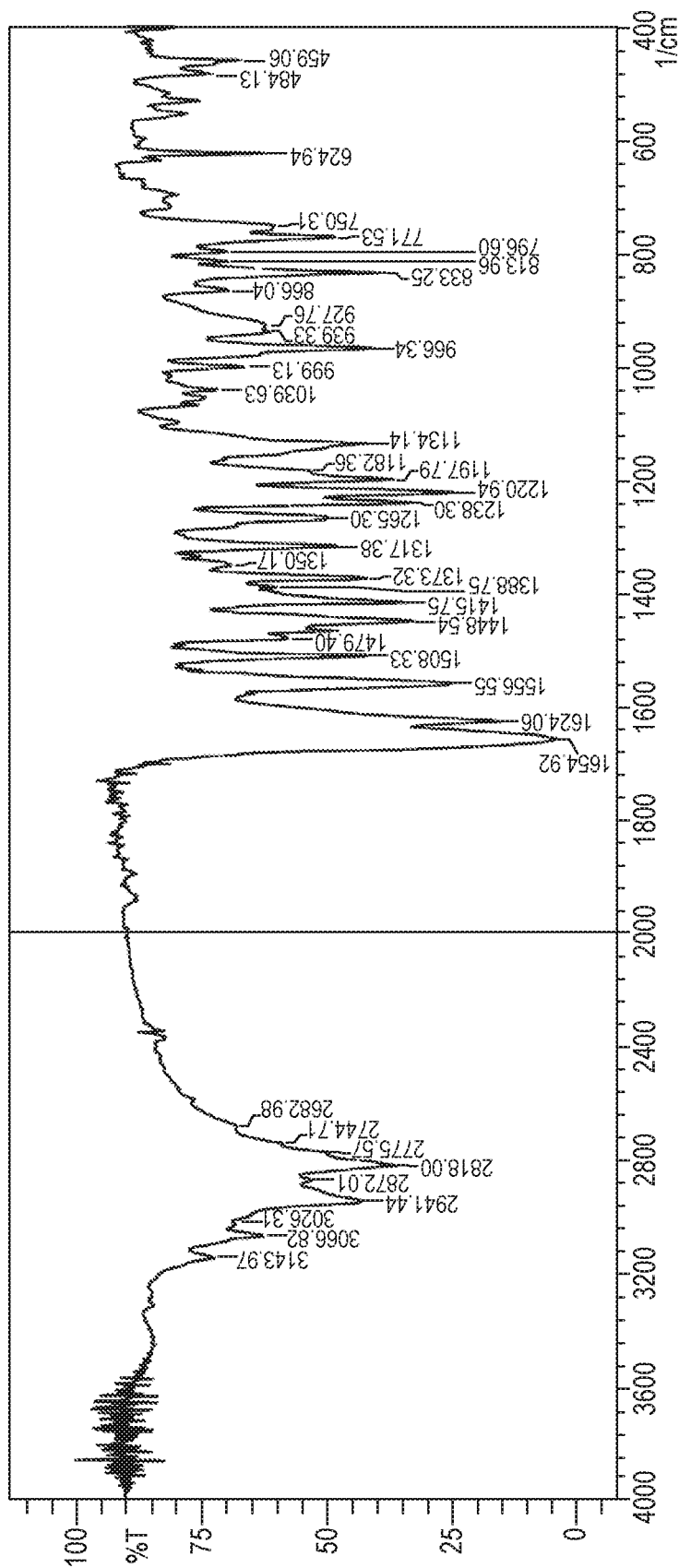
FIG. 12 shows the infrared absorption spectrum of the anhydride of the benzothiophene compound synthesized in Production Example 4.

The IR (KBr) spectrum of the anhydride obtained above was measured in the same manner as in Production Example 2. FIG. 12 shows the IR (KBr) spectrum. As shown in FIG. 12, the 7-[4-(4-benzo[b]thiophen-4-yl-piperazin-1-yl)butoxy]-1H-quinolin-2-one had absorption bands in the IR (KBr) spectrum in the vicinity of wavenumbers 2941 $cm^{-1}$, 2818 $cm^{-1}$, 1655 $cm^{-1}$, 1624 $cm^{-1}$, 1449 $cm^{-1}$, 1221 $cm^{-1}$, and 833 $cm^{-1}$.

The water content of the anhydride synthesized by the aforesaid method was measured in the same manner as in Production Example 2. The results revealed that the anhydride obtained above had a water content of 0.04% by weight.

Injectable Preparation

Injectable preparations described below were produced using a dihydrate of Compound (I) (the dihydrate obtained in Production Example 1 was ground into a desirable particle size) or an anhydride of Compound (I), both produced by the method described above, and the following components. Unless otherwise defined, dihydrate of Compound (I), and anhydrate of Compound (I) were used after being ground into 2 to 6 μm. The particle size was measured using a laser diffraction particle size analyzer (SALD-3000) or SALD-3100, produced by Shimadzu Corporation). When an injectable preparation contains 108 mg of dihydrate of Compound (I) per 1 mL of the preparation, 100 mg of Compound (I) is contained in the injectable preparation.

Polyethylene glycol 400 (Macrogol 400, produced by Wako Pure Chemical Industries)
Sodium chloride (produced by Nacalai Tesque, Inc.)
Sodium dihydrogenphosphate dihydrate (produced by Nacalai Tesque, Inc.)
Disodium hydrogenphosphate dodecahydrate (produced by Wako Pure Chemical Industries)
Polyoxyethylene sorbitan mono-fatty acid ester (polysorbate 80, produced by NOF Corporation)
DL-methionine (produced by Wako Pure Chemical Industries)
Polyoxyethylene (160) polyoxypropylene (30) glycol (Pluronic F68, produced by BASF Japan Ltd.)
Sodium hydroxide (produced by Wako Pure Chemical Industries)
Sorbitol (D(−)-sorbitol, produced by Wako Pure Chemical Industries)
Sodium carboxymethylcellulose (Sodium carboxymethyl cellulose, produced by Hercules Chemical Co., Ltd.)
Benzyl benzoate (produced by Nacalai Tesque, Inc.)

Example 1: Synthesis of Injectable Preparation Comprising an Aqueous Particle Binder-Containing Anhydride of Compound (I) as an Active Ingredient Polyethylene glycol 400 (8640 mg), polyoxyethylene (160) polyoxypropylene (30) glycol (300 mg), sodium chloride (12000 mg), DL-methionine (750 mg), sodium dihydrogenphosphate dihydrate (226 mg), disodium hydrogenphosphate dodecahydrate (176 mg), and polysorbate 80 (90 mg) were, as a vehicle, weighed and mixed in a 500 mL beaker. Water for injection (240 mL) was added to dissolve the vehicle. After confirming that the vehicle was completely dissolved in the water for injection, the resulting solution was made to pass through a polyethersulfone (PES) filter (Millipore Express PLUS high flow rate, 73 mm/0.22 μm, SCGP U11 RE, produced by Nihon Millipore K. K.) in a clean bench (biological clean bench, MCV-B161F, produced by Biomedix). An anhydride of Compound (I) (30000 mg) was added to the solution that had been passed through the filter in the clean bench to make a suspension. The mixture was adjusted to have a pH value of about 7 using a 1N or 5N sodium hydroxide that had been passed through a PES filter. The volume of the resulting solution was measured using a measuring cylinder, and a portion thereof (0.5 mL) was extracted. After measuring the content of Compound (I) by the HPLC method, water for injection was added thereto to adjust the concentration of Compound (I) to 100 mg/mL.

Thereafter, each formulation was individually placed in a vial (φ23×35 and an opening of 13 mm, produced by Iwata Glass Industrial Co., Ltd.), and then processed in an autoclave (121° C., 20 minutes) to obtain an injectable preparation. The resulting injectable preparation had a pH value of 6.54.

The particle diameter of the anhydride of Compound (I) contained in the resulting injectable preparation was measured using a laser diffraction particle size analyzer (SALD- 3000) or SALD-3100, produced by Shimadzu Corporation). Specifically, the secondary mean particle diameter was defined as the particle diameter measured using a circulation cell and using water as the measurement medium. The mean primary particle diameter was defined as the particle diameter measured under the same conditions as described above except that the measurement was performed while the measurement medium was subjected to ultrasonic irradiation. (This is also true for the Examples described below.) The anhydride of Compound (I) had a secondary mean particle diameter of 10.480 µm. It was confirmed that particles of the anhydride of Compound (I) aggregated to form secondary particles.

Example 2: Synthesis of Injectable Preparation Comprising Aqueous Particle Binder-Containing Dihydrate of Compound (I) as an Active Ingredient An injectable preparation was produced in the same manner as in Example 1, except that dihydrate of Compound (I) was used instead of anhydride of Compound (I) and the autoclave process was not performed. The resulting injectable preparation had a pH value of 7.08.

The particle diameter of the dihydrate of Compound (I) contained in the resulting injectable preparation was measured in the same manner as in Example 1. The dihydrate of Compound (I) had a mean particle diameter of 9.819 µm. It was confirmed that particles of the dihydrate of Compound (I) aggregated to form secondary particles.

Components of the injectable preparations obtained in Examples 1 and 2, and the amount of each component therein (i.e., the formulations of injectable preparations), are shown in Table 1 below.

TABLE 1

| Components | Amount (mg) | |
|---|---|---|
| | Example 1 | Example 2 |
| Anhydride of Compound (I) | 100 | — |
| Dihydrate of Compound (I) | — | 108 |
| Polyethylene glycol 400 | 28.8 | 28.8 |
| Sodium chloride | 40 | 5 |
| Sodium dihydrogenphosphate dihydrate | 0.756 | 0.756 |
| Disodium hydrogenphosphate dodecahydrate | 0.588 | 0.588 |
| Polysorbate 80 | 0.3 | 0.3 |
| DL-methionine | 2.5 | 2.5 |
| Polyoxyethylene (160) polyoxypropylene (30) glycol | 1 | 1 |
| Sodium hydroxide | Q.S. | Q.S. |
| Water for injection | Q.S. | Q.S. |
| Total | 1 mL | 1 mL |

The injectable preparation of Example 2 was re-produced in the same manner (Example 2b). At the same time, an injectable preparation (Example 2c) using 10 mg/mL of sodium chloride instead of 5 mg/mL, and an injectable preparation (Example 2a) excluding polyethylene glycol from Example 2c were produced. Specifically, injectable preparations (Examples 2a, 2b, and 2c) as shown in Table 2 were produced. Furthermore, injectable preparations of Examples 2a, 2b, and 2c were allowed to stand at 60° C. for one month and then their dispersibility and redispersibility were analyzed. The mean primary particle diameter and mean secondary particle diameter were measured before and after standing. Table 2 also shows the results.

TABLE 2

| Components | Amount (mg) | | |
|---|---|---|---|
| | 2a | 2b | 2c |
| Dihydrate of Compound (I) | 108 | 108 | 108 |
| Polyethylene glycol 400 | — | 28.8 | 28.8 |
| Sodium chloride | 10 | 5 | 10 |
| Sodium dihydrogenphosphate dihydrate | 0.756 | 0.756 | 0.756 |
| Disodium hydrogenphosphate dodecahydrate | 0.588 | 0.588 | 0.588 |
| Polysorbate 80 | 0.3 | 0.3 | 0.3 |
| DL-methionine | 2.5 | 2.5 | 2.5 |
| Polyoxyethylene (160) polyoxypropylene (30) glycol | 1 | 1 | 1 |
| Sodium hydroxide | | Q.S. | |
| Water for injection | | Q.S. | |
| pH | | 7.0 | |
| Total | | 1 mL | |
| Dispersibility (60° C./1M, Rf) | 0.72 | 0.67 | 0.78 |
| Redispersibility (60° C./1M) | A | A | A |
| Mean particle diameter (Initial, µm) Upper column/Primary particle, Lower column/Secondary particle | 4.4 9.8 | 5.0 10.3 | 4.9 8.9 |
| Mean particle diameter (60° C./1M, µm) Upper column/Primary particle, Lower column/Secondary particle | 3.9 10.3 | 3.8 10.4 | 4.2 10.8 |

In the Table, the values shown in the column of "Dispersibility (60° C./1M, Rf)" indicate the multiple of the precipitation height formed upon allowing each injectable preparation to stand at 60° C. for one month after production relative to the liquid surface height. Specifically, the numbers indicate the ratio of the precipitation height when the height of the liquid surface defined as 1. (60° C./1M means that the sample was allowed to stand at 60° C. for one month).

Furthermore, the "A" symbol in the column "Redispersibility (60° C./1M)" indicates that the injectable preparation easily returned to a suspension when gently shaken by hand after precipitation had occurred due to standing at 60° C. for one month.

Example 3: Synthesis of Injectable Preparation Comprising an Oily Particle Binder-Containing Anhydride of Compound (I) as an Active Ingredient Carboxymethylcellulose was weighed (15000 mg) and placed in a 300 mL beaker. Water for injection (120 mL) was added thereto, and the carboxymethylcellulose was dissolved using a homogenizer (OMNI TH, produced by OMNI International Co., Ltd.) at 50° C. Subsequently, sorbitol (75000 mg), sodium dihydrogenphosphate dihydrate (117 mg), and polysorbate 80 (150 mg) were weighed and added into the 300 mL beaker. The mixture was then fully stirred. After dissolving the resulting solution was passed through a polyethersulfone (PES) filter (Millipore Express PLUS high flow rate, 73 mm/0.22 µm, SCGP U11 RE, produced by Nihon Millipore K.K.) in a clean bench (biological clean bench, MCV-B161F, Biomedix, produced by Biomedix). In the clean bench, benzyl benzoate that had been passed through a polytetrafluoroethylene (PTFE) filter (Millex®-FG, 0.2 µm, 25 mm, produced by Nihon Millipore K.K., sterilized by ethylene oxide) was added to the 10 mL-line of a measuring flask whose tare weight was weighed in advance. Then, the weight of the measuring flask was measured. The amount of benzyl benzoate necessary to add was estimated based on the density calculated from the weight measured. The necessary amount of benzyl benzoate was added to the solution passed through a PES filter, and then fully mixed. An anhydride of Compound (I) (16215 mg) weighed in the clean bench was added thereto. The mixture was adjusted to have a pH value of about 7 using a 1N or 5N sodium hydroxide that had been passed through a PES filter. The volume thereof was measured using a measuring cylinder, and a portion thereof (0.5 mL) was extracted. After measuring the content of Compound (I) by the HPLC method, water for injection was added thereto to adjust the concentration of Compound (I) to 100 mg/mL. The resulting injectable preparation had a pH value of 6.95.

The particle diameter of the anhydride of Compound (I) contained in the resulting injectable preparation was measured in the same manner as in Example 1. The anhydride of Compound (I) had a mean particle diameter of 13.237 μm. It was confirmed that particles of the anhydride of Compound (I) aggregated to form secondary particles.

Example 4: Synthesis of Injectable Preparation Comprising an Oily Particle Binder-Containing Dihydrate of Compound (I) as an Active Ingredient An injectable preparation was produced in the same manner as in Example 3, except that a dihydrate of Compound (I) was used instead of an anhydride of Compound (I). The resulting injectable preparation had a pH value of 7.06.

The particle diameter of the dihydrate of Compound (I) contained in the resulting injectable preparation was measured in the same manner as in Example 1. The dihydrate of Compound (I) had a mean particle diameter of 8.025 μm. It was confirmed that particles of the dihydrate of Compound (I) aggregated to form secondary particles.

Components of the injectable preparations obtained in Examples 3 and 4, and the amount of each component therein, are shown in Table 3 below.

TABLE 3

| | Amount (mg) | |
|---|---|---|
| Components | Example 3 | Example 4 |
| Anhydride of Compound (I) | 100 | — |
| Dihydrate of Compound (I) | — | 108 |
| Sorbitol | 50 | 45 |
| Sodium carboxymethylcellulose | 10 | 10 |
| Sodium dihydrogenphosphate dihydrate | 0.78 | 0.624 |
| Disodium hydrogenphosphate dodecahydrate | — | 2.148 |
| Benzyl benzoate | 0.3 | 0.8 |
| Polysorbate 80 | 1 | 1 |
| Sodium hydroxide | Q.S. | Q.S. |
| Water for injection | Q.S. | Q.S. |
| Total | 1 mL | 1 mL |

The injectable preparation of Example 4 was then re-produced in the same manner (Example 4b). At the same time, injectable preparations were produced in the same manner except that benzyl benzoate was used in an amount of 0.6 mg/mL (Example 4a) or 1.0 mg/mL (Example 4c) instead of 0.8 mg/mL. Specifically, the injectable preparations (Examples 4a, 4b, and 4c) shown in Table 4 were produced. Furthermore, injectable preparations of Examples 4a, 4b, and 4c were allowed to stand at 60° C. for one month, and then their dispersibility and redispersibility were analyzed. The mean primary particle diameter and mean secondary particle diameter were measured before and after standing. Table 4 also shows the results.

TABLE 4

| | | | Amount (mg) | | |
|---|---|---|---|---|---|
| Components | | | 4a | 4b | 4c |
| Dihydrate of Compound (I) | | | 108 | 108 | 108 |
| Sorbitol | | | 45 | 45 | 45 |
| Sodium carboxymethylcellulose | | | 10 | 10 | 10 |
| Sodium dihydrogenphosphate dihydrate | | | 0.624 | 0.624 | 0.624 |
| Disodium hydrogenphosphate dodecahydrate | | | 2.148 | 2.148 | 2.148 |
| Benzyl benzoate | | | 0.6 | 0.8 | 1 |
| Polysorbate 80 | | | 1 | 1 | 1 |
| Sodium hydroxide | | | | Q.S. | |
| Water for injection | | | | Q.S. | |
| pH | | | | 7.0 | |
| Total | | | | 1 mL | |
| Dispersibility (60° C./1M, Rf value) | | | 0.64 | 0.80 | 0.73 |
| Redispersibility (60° C./1M) | | | A | A | A |
| Mean particle diameter (Initial, μm) | Primary | | 3.9 | 3.8 | 3.7 |
| | Secondary | | 8.0 | 7.6 | 7.5 |
| Mean particle diameter (60° C./1M, μm) | Primary | | 4.3 | 4.4 | 4.4 |
| | Secondary | | 11.9 | 11.6 | 11.6 |

The recitations in the columns in the Table above are the same as those in Table 2.

The injectable preparations of Examples 1 and 3 were re-produced (Examples 1a and 3a), and the mean particle diameters thereof were measured. The results revealed that the injectable preparation of Example 1a had a mean primary particle diameter of 5.0 μm and a mean secondary particle diameter of 10.3 μm, and the injectable preparation of Example 3a had a mean primary particle diameter of 3.9 μm and a mean secondary particle diameter of 15.1 μm.

Example 5

An injectable preparation was produced in the same manner as in Example 3 except that a dihydrate of Compound (I) was used instead of an anhydride of Compound (I), benzyl alcohol (10 mg/mL) was used instead of benzyl benzoate (0.3 mg/mL). The secondary mean particle diameter of the dihydrate of Compound (I) in the injectable preparation was 6.9 μm and the mean primary particle diameter thereof was 2.3 μm. From this result, it was confirmed that particles of the dihydrate of Compound (I) aggregated to form secondary particles. When the injectable preparation was allowed to stand for four days at room temperature, precipitation occurred but easily returned to a suspension when gently shaken by hand.

Test Examples 1 and 2

The injectable preparations comprising an anhydride of Compound (I) or a dihydrate of Compound (I) produced in Examples 1 to 4 as an active ingredient were each injected into the crural muscle of male rats at a dose of 25 mg/kg. To evaluate the transfer of Compound (I) into the blood after administration, blood samples were collected 0.25, 1, 3, 6, 9, 14, 21, and 28 days after administration, and the concentration of Compound (I) in the blood of each sample was measured.

Figure 13:
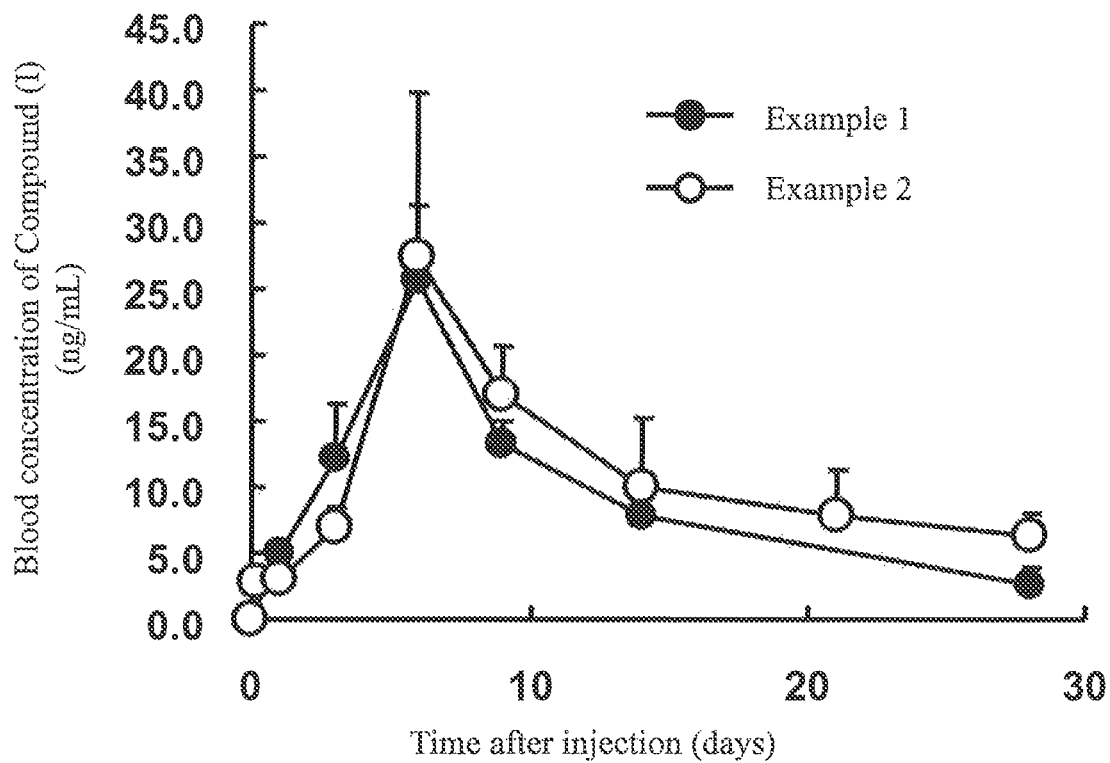
FIG. 13 is a graph showing the mean blood concentration-time profiles obtained in Test Example 1 in which the injectable preparations containing Compound (I) of Examples 1 and 2 as an active ingredient were administered to rats.
Figure 14:
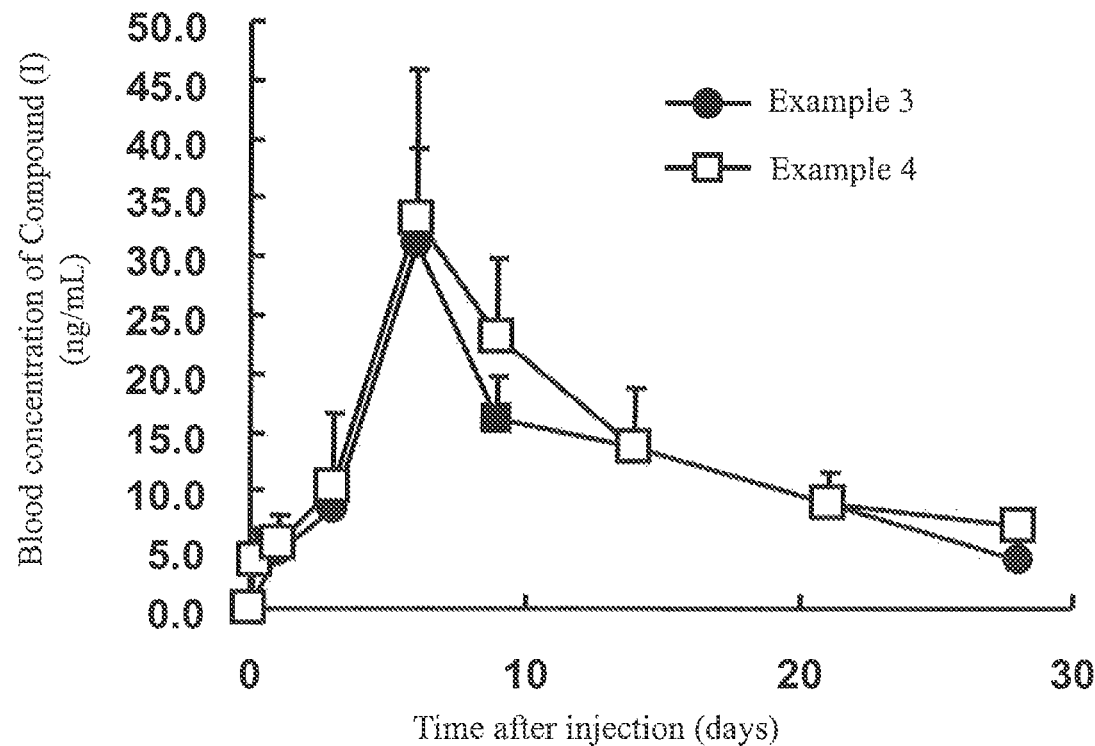
FIG. 14 is a graph showing the mean blood concentration-time profiles obtained in Test Example 2 in which the injectable preparations containing Compound (I) of Examples 3 and 4 as an active ingredient were administered to rats.

FIG. 13 shows the mean blood concentration-time profiles obtained by administering the injectable preparations produced in Examples 1 and 2. FIG. 14 shows the mean blood concentration-time profiles obtained by administering the injectable preparations produced in Examples 3 and 4. As is clear from FIGS. 13 and 14, in either case in which the injectable preparation comprising an anhydride or dihydrate of Compound (I) was administered, an effective blood concentration of Compound (I) was sustained for at least 28 days. In particular, the results of Test Example 2 (FIG. 14) revealed that when an injectable preparation containing a dihydrate of Compound (I) produced in Example 4 was administered, an excessive increase in blood concentration was not observed, and a stable blood concentration was obtained.

Test Example 3

The injectable preparations (Example A and Example B) shown in Table 5 were produced in the same manner as in Examples 3 and 4, respectively.

TABLE 5

| Components | Amount (mg) | |
| --- | --- | --- |
| | Example A | Example B |
| Anhydride of Compound (I) | 100 | — |
| Dihydrate of Compound (I) | — | 108 |
| Sorbitol | 50 | 50 |
| Sodium carboxymethylcellulose | 10 | 10 |
| Sodium dihydrogenphosphate dihydrate | 0.78 | 0.78 |
| Benzyl benzoate | 1 | 0.8 |
| Polysorbate 80 | 1 | 1 |
| Sodium hydroxide | Q.S. (adjusted to pH 7) | Q.S. (adjusted to pH 7) |
| Water for injection | Q.S. | Q.S. |
| Total | 1 mL | 1 mL |

The freeze-dried injectable preparations (Comparative Example A and Comparative Example B) shown in Table 6 below were produced using the same method as disclosed in the Example of JP2012-232958A. (The content of JP2012-232958A is incorporated in this specification by reference.) The injectable preparations were produced at a 100-mL scale.

TABLE 6

| Components | Amount (mg) | |
| --- | --- | --- |
| | Comparative Example A | Comparative Example B |
| Anhydride of Compound (I) | 100 | — |
| Dihydrate of Compound (I) | — | 108 |
| Mannitol | 41.6 | 41.6 |
| Sodium carboxymethylcellulose | 8.32 | 8.32 |
| Sodium dihydrogenphosphate dihydrate | 0.78 | 0.624 |
| Sodium hydroxide | Q.S. (adjusted to pH 7) | Q.S. (adjusted to pH 7) |
| Water for injection | Q.S. | Q.S. |
| Total | 1 mL | 1 mL |

The injectable preparations of Example A, Example B, Comparative Example A, and Comparative Example B were each injected into the crural muscle of male rats at a Compound (I) dose of 25 mg/kg. To evaluate the transfer of Compound (I) into the blood after administration, blood samples were collected 0.25, 1, 3, 6, 9, 14, 21, and 28 days after administration, and the concentration of Compound (I) in the blood of each sample was measured. The freeze-dried injectable preparations of Comparative Examples A and B are such that Compound (I) or a salt thereof does not form secondary particles.

Figure 15:
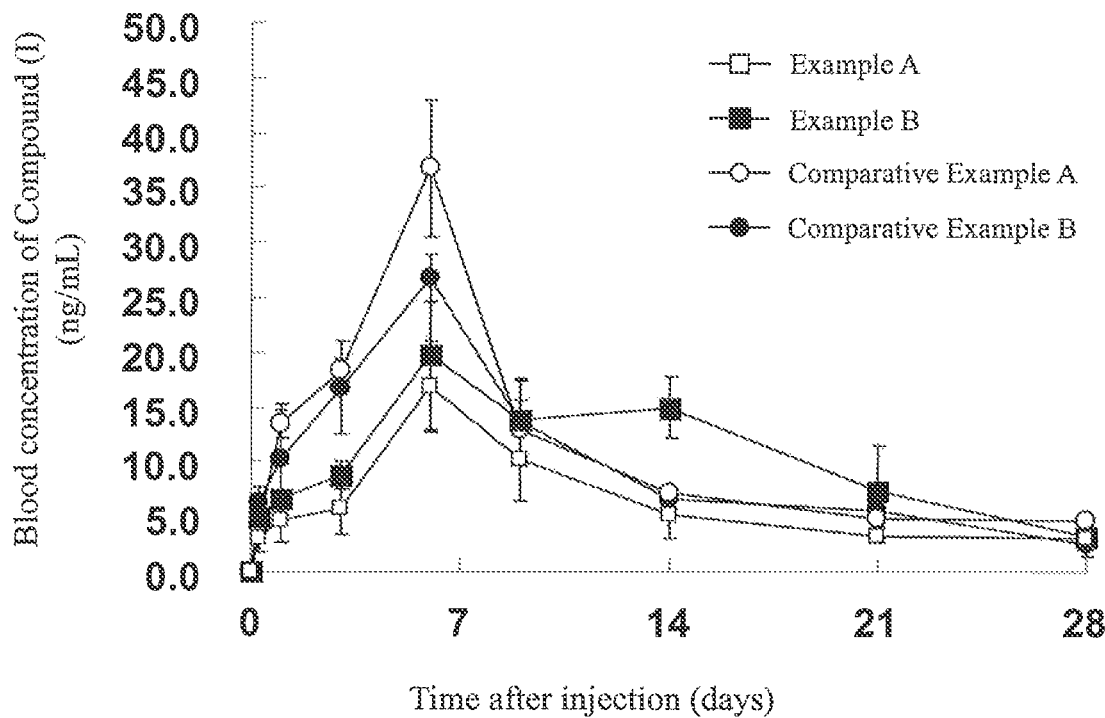
FIG. 15 is a graph showing the mean blood concentration-time profiles obtained in Test Example 3 in which the injectable preparations of Example A, Example B, Comparative Example A, and Comparative Example B were administered to rats.

FIG. 15 shows the obtained results in the form of a graph. From FIG. 15, it was confirmed that, compared to the case in which secondary particles are not formed, the injectable preparation of the present invention wherein Compound (I) or a salt thereof forms secondary particles with a specific particle diameter leads to a suppression of the burst phenomenon after the start of administration and renders excellent sustainability of medicinal efficacy.

Test Example 4

The injectable preparations having the compositions shown in Table 7 (Examples C to F) were produced in the same manner as in Example 2.

TABLE 7

| Components | Amount (mg) | | | |
| --- | --- | --- | --- | --- |
| | Example C | Example D | Example E | Example F |
| Dihydrate of Compound (I) | 108 | 108 | 108 | 108 |
| Sodium dihydrogenphosphate dihydrate | 0.756 | 0.756 | 0.756 | 0.756 |
| Disodium hydrogenphosphate dodecahydrate | 0.588 | 0.588 | 0.588 | 0.588 |
| Polysorbate 80 | 0.3 | 0.3 | 0.3 | 0.3 |
| Sodium chloride | 10 | 5 | 10 | 5 |
| DL-methionine | 2.5 | 2.5 | — | — |
| Polyoxyethylene (160) polyoxypropylene (30) glycol | 1 | 1 | 1 | 1 |
| Polyethylene glycol 400 | — | 28.8 | — | 28.8 |
| Sodium hydroxide | Q.S. (pH 7.0) | Q.S. (pH 7.0) | Q.S. (pH 7.0) | Q.S. (pH 7.0) |
| Water for injection | Q.S. | Q.S. | Q.S. | Q.S. |
| Total | 1 mL | 1 mL | 1 mL | 1 mL |

The injectable preparations of Examples C to F were each injected into the crural muscle of male rats at a Compound (I) dose of 25 mg/kg. To evaluate the transfer of Compound (I) into the blood after administration, blood samples were collected 0.25, 1, 3, 6, 9, 14, 21, and 28 days after administration, and the concentration of Compound (I) in the blood of each sample was measured.

Figure 16:
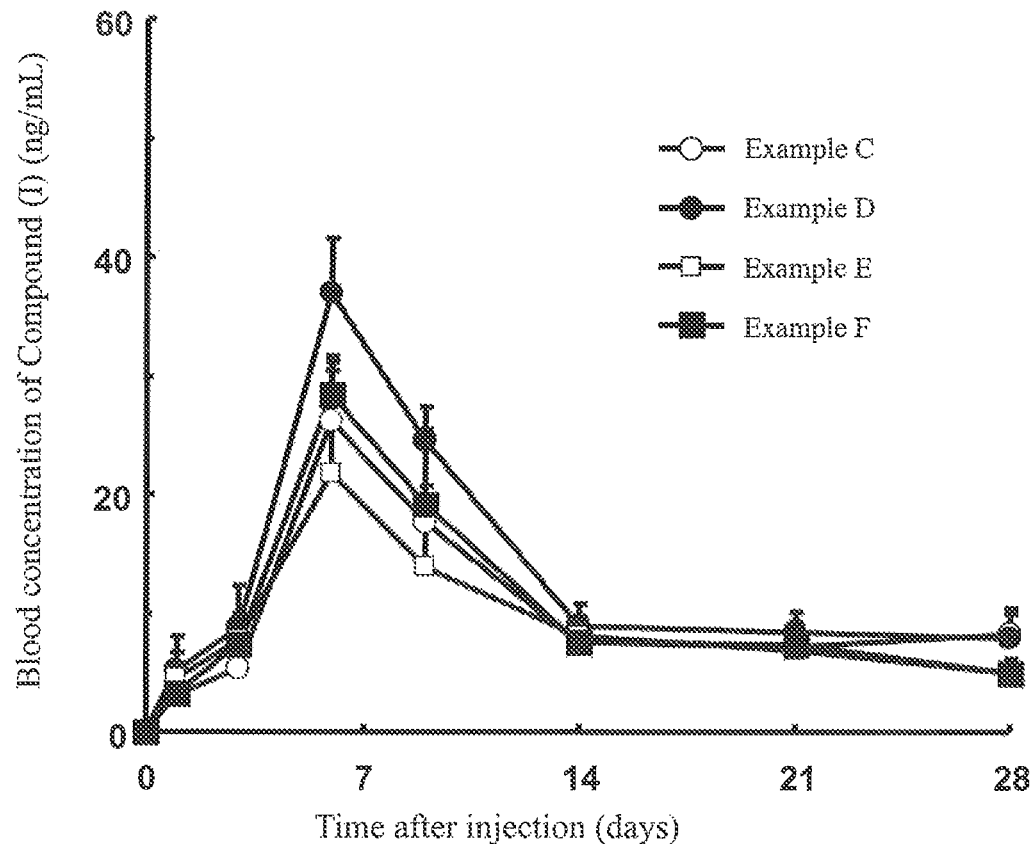
FIG. 16 is a graph showing the mean blood concentration-time profiles obtained in Test Example 4 in which the injectable preparations of Examples C to F were administered to rats.

FIG. 16 shows the obtained results in a form of a graph. Table 8 shows $C_{max}$ and $AUC_{28\ day}$ after administering an injectable preparation of each Example.

TABLE 8

| Formulation | $C_{max}$ (ng/mL) | $AUC_{28\ day}$ (ng · day/mL) |
|---|---|---|
| Example C | 26.2 ± 4.9 | 290.9 ± 43.3 |
| Example D | 36.9 ± 4.6 | 377.0 ± 26.9 |
| Example E | 21.7 ± 8.7 | 259.1 ± 75.2 |
| Example F | 28.3 ± 3.4 | 299.5 ± 21.9 |

Mean ± SD

From the results shown above, it was confirmed that the blood concentration of Compound (I) was maintained for a month from the time of administration for all of the injectable preparations of Examples C to F.

Test Example 5

Each vehicle component was dissolved in water for injection in the same manner as in Example 2. A dihydrate of Compound (I) was suspended in the resulting injectable solutions to obtain injectable preparations (Examples G-1 to G-6, Examples H-1 to H-6, Example I-1 to I-6, and Examples J-1 to J-6) having the formulations shown in Tables 9 to 12.

TABLE 9

Examples G series

| | Amount (mg) | | | | | |
|---|---|---|---|---|---|---|
| | G-1 | G-2 | G-3 | G-4 | G-5 | G-6 |
| Dihydrate of Compound (I) | 108 | 108 | 108 | 108 | 108 | 108 |
| Macrogol 400 | 28.8 | 28.8 | 28.8 | 28.8 | 28.8 | 28.8 |
| Sodium hydroxide | 5 | 5 | 5 | 5 | 5 | 5 |
| Sodium dihydrogenphosphate dihydrate | 0.756 | 0.756 | 0.756 | 0.756 | 0.756 | 0.756 |
| Disodium hydrogenphosphate dodecahydrate | 0.588 | 0.588 | 0.588 | 0.588 | 0.588 | 0.588 |
| Polysorbate 80 | 0.3 | 0.3 | 0.3 | 0.3 | 0.3 | 0.3 |
| Polyoxyethylene (160) polyoxypropylene (30) glycol | 0 | 0.1 | 0.3 | 1 | 3 | 10 |
| Sodium hydroxide | Q.S. (adjusted to pH 7) | Q.S. (adjusted to pH 7) | Q.S. (adjusted to pH 7) | Q.S. (adjusted to pH 7) | Q.S. (adjusted to pH 7) | Q.S. (adjusted to pH 7) |
| Water for injection | Q.S. | Q.S. | Q.S. | Q.S. | Q.S. | Q.S. |
| Total | 1 mL | 1 mL | 1 mL | 1 mL | 1 mL | 1 mL |

TABLE 10

Examples H series

| | Amount (mg) | | | | | |
|---|---|---|---|---|---|---|
| | H-1 | H-2 | H-3 | H-4 | H-5 | H-6 |
| Dihydrate of Compound (I) | 108 | 108 | 108 | 108 | 108 | 108 |
| Macrogol 400 | 28.8 | 28.8 | 28.8 | 28.8 | 28.8 | 28.8 |
| Sodium chloride | 5 | 5 | 5 | 5 | 5 | 5 |
| Sodium dihydrogenphosphate dihydrate | 0.756 | 0.756 | 0.756 | 0.756 | 0.756 | 0.756 |
| Disodium hydrogenphosphate dodecahydrate | 0.588 | 0.588 | 0.588 | 0.588 | 0.588 | 0.588 |
| Polysorbate 80 | 0 | 0 | 0 | 0 | 0 | 0 |
| Polyoxyethylene (160) polyoxypropylene (30) glycol | 0 | 0.1 | 0.3 | 1 | 3 | 10 |
| Sodium hydroxide | Q.S. (adjusted to pH 7) | Q.S. (adjusted to pH 7) | Q.S. (adjusted to pH 7) | Q.S. (adjusted to pH 7) | Q.S. (adjusted to pH 7) | Q.S. (adjusted to pH 7) |
| Water for injection | Q.S. | Q.S. | Q.S. | Q.S. | Q.S. | Q.S. |
| Total | 1 mL | 1 mL | 1 mL | 1 mL | 1 mL | 1 mL |

TABLE 11

Examples I series

| | Amount (mg) | | | | | |
|---|---|---|---|---|---|---|
| | I-1 | I-2 | I-3 | I-4 | I-5 | I-6 |
| Dihydrate of Compound (I) | 108 | 108 | 108 | 108 | 108 | 108 |
| Macrogol 400 | 0 | 0 | 0 | 0 | 0 | 0 |
| Sodium chloride | 5 | 5 | 5 | 5 | 5 | 5 |
| Sodium dihydrogenphosphate dihydrate | 0.756 | 0.756 | 0.756 | 0.756 | 0.756 | 0.756 |
| Disodium hydrogenphosphate dodecahydrate | 0.588 | 0.588 | 0.588 | 0.588 | 0.588 | 0.588 |
| Polysorbate 80 | 0.3 | 0.3 | 0.3 | 0.3 | 0.3 | 0.3 |
| Polyoxyethylene (160) polyoxypropylene (30) glycol | 0 | 0.1 | 0.3 | 1 | 3 | 10 |
| Sodium hydroxide | Q.S. (adjusted to pH 7) | Q.S. (adjusted to pH 7) | Q.S. (adjusted to pH 7) | Q.S. (adjusted to pH 7) | Q.S. (adjusted to pH 7) | Q.S. (adjusted to pH 7) |
| Water for injection | Q.S. | Q.S. | Q.S. | Q.S. | Q.S. | Q.S. |
| Total | 1 mL | 1 mL | 1 mL | 1 mL | 1 mL | 1 mL |

TABLE 12

Examples J series

| | Amount (mg) | | | | | |
|---|---|---|---|---|---|---|
| | J-1 | J-2 | J-3 | J-4 | J-5 | J-6 |
| Dihydrate of Compound (I) | 108 | 108 | 108 | 108 | 108 | 108 |
| Macrogol 400 | 0 | 0 | 0 | 0 | 0 | 0 |
| Sodium chloride | 5 | 5 | 5 | 5 | 5 | 5 |
| Sodium dihydrogenphosphate dihydrate | 0.756 | 0.756 | 0.756 | 0.756 | 0.756 | 0.756 |
| Disodium hydrogenphosphate dodecahydrate | 0.588 | 0.588 | 0.588 | 0.588 | 0.588 | 0.588 |
| Polysorbate 80 | 0 | 0 | 0 | 0 | 0 | 0 |
| Polyoxyethylene (160) polyoxypropylene (30) glycol | 0 | 0.1 | 0.3 | 1 | 3 | 10 |
| Sodium hydroxide | Q.S. (adjusted to pH 7) | Q.S. (adjusted to pH 7) | Q.S. (adjusted to pH 7) | Q.S. (adjusted to pH 7) | Q.S. (adjusted to pH 7) | Q.S. (adjusted to pH 7) |
| Water for injection | Q.S. | Q.S. | Q.S. | Q.S. | Q.S. | Q.S. |
| Total | 1 mL | 1 mL | 1 mL | 1 mL | 1 mL | 1 mL |

Table 13 shows the Rf value (the precipitation height when the height of the liquid surface defined as 1) of each Example.

The Rf values were measured after allowing each Example to stand at room temperature for five days while applying vibration. The test tube and vibration tester used for the measurement are as follows.

Test Tube into which Each Example was Filled

A test tube equipped with a screw top (NR-10, manufactured by Maruemu Corporation), Material (Body): Borosilicate glass, Length: 105 mm, Shape: Round bottom, Capacity: 12 mL, External diameter ($\phi$)×Total height: $\phi$16.5 mm×105 mm Vibration Tester on which Each Test Tube was Placed Air handling unit DH-14, manufactured by Sinko Industries Ltd.

(The air handling unit was used as a vibration tester by placing thereon each test tube containing an injectable preparation.)

The vibration levels of the air handling unit were measured using a vibration level meter (VM-53A, manufactured by RION Co., Ltd.), and the following vibration levels were observed:

X-axis direction: 68 dB, Y-axis direction: 76 dB, and Z-axis direction: 90 dB.

Application of vibration is considered to make the precipitate denser, facilitating the formation of a hard cake. Therefore, the conditions for the measurement of Rf value described above are more severe than standing still.

Figure 17:
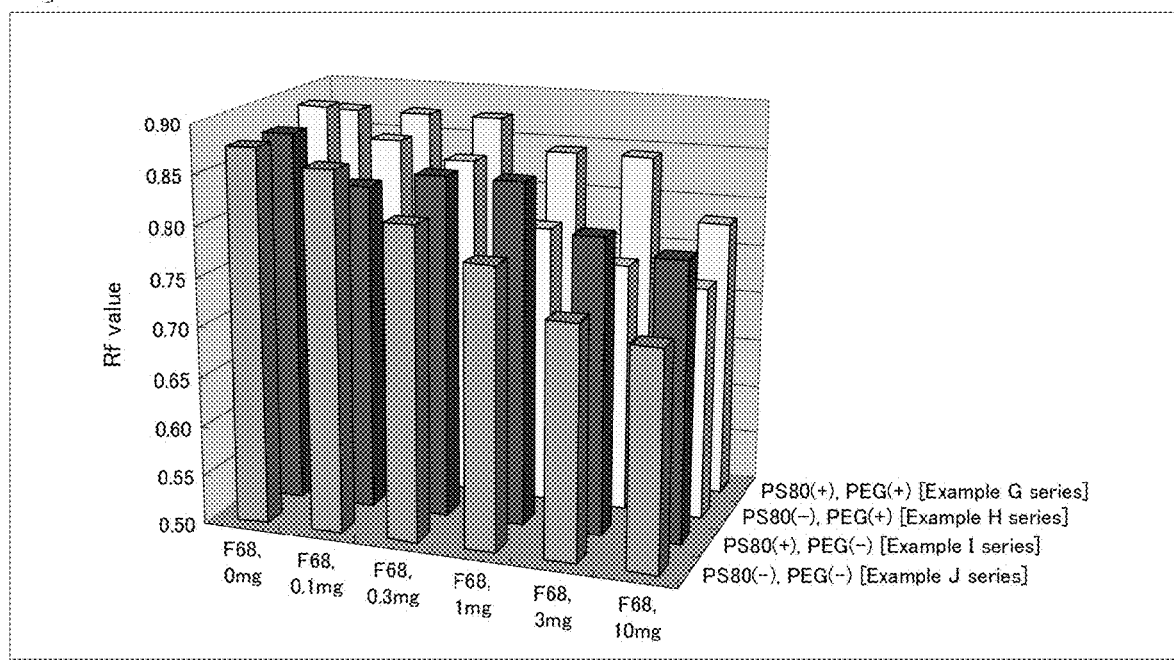
FIG. 17 is a graph showing the Rf values of an injectable preparation of each Example measured in Test Example 5.

FIG. 17 is a graph showing the results of Table 13. In Table 13 and FIG. 17, PS80 stands for Polysorbate 80, PEG stands for Macrogol 400, and F68 stands for polyoxyethylene (160) polyoxypropylene (30) glycol (Pluronic F68). The symbol (+) appearing after some components means that the component was contained therein, and the (−) indicates that the component was not contained therein. This is also applicable to Table 14 shown below.

TABLE 13

|  | F68, 0 mg | F68, 0.1 mg | F68, 0.3 mg | F68, 1 mg | F68, 3 mg | F68, 10 mg |
|---|---|---|---|---|---|---|
| PS80(−), PEG(−) [Example J Series] | 0.88 | 0.86 | 0.81 | 0.78 | 0.73 | 0.72 |
| PS80(+), PEG(−) [Example I Series] | 0.88 | 0.83 | 0.84 | 0.84 | 0.80 | 0.78 |
| PS80(−), PEG(+) [Example H Series] | 0.89 | 0.86 | 0.84 | 0.78 | 0.75 | 0.73 |
| PS80(+), PEG(+) [Example G Series] | 0.88 | 0.88 | 0.88 | 0.84 | 0.84 | 0.78 |

Test Example 6

The syringability of the injectable preparations of Examples G-1 to G-6, Examples H-1 to H-6, Examples I-1 to I-6, and Examples J-1 to J-6 was evaluated as described below.

After production, the injectable preparations of Examples G-1 to G-6, Examples H-1 to H-6, Examples I-1 to I-6, and Examples J-1 to J-6 were allowed to stand for five days while vibration was applied. Thereafter, the injectable preparations of Examples G-1 to G-6, Examples H-1 to H-6, Examples I-1 to I-6, and Examples J-1 to J-6 were inverted to redisperse the precipitates therein. The precipitates in all of the injectable preparations were preferably redispersed by being inverted only once.

Thereafter, 500 µL of each injectable preparation was filled in a syringe equipped with a needle (27 G×1.5 inch, manufactured by Terumo Corporation), and then the injectability of each injectable preparation into extracted muscle (chicken thigh) was confirmed. Table 14 shows the results. In Table 14, "a" indicates that the entire quantity of the injectable preparation could be injected (i.e., the syringability was satisfactory); and "b" indicates that clogging of the syringe needle occurred, and that the quantity of the injectable preparation could not be injected in its entirety.

TABLE 14

|  | F68, 0 mg | F68, 0.1 mg | F68, 0.3 mg | F68, 1 mg | F68, 3 mg | F68, 10 mg |
|---|---|---|---|---|---|---|
| PS80(−), PEG(−) [Example J Series] | b | b | a | a | a | a |
| PS80(+), PEG(−) [Example I Series] | b | a | a | a | a | a |
| PS80(−), PEG(+) [Example H Series] | a | a | a | a | a | a |
| PS80(+), PEG(+) [Example G Series] | a | a | a | a | a | a |

The invention claimed is:

1. An injectable preparation comprising 7-[4-(4-benzo[b]thiophen-4-yl-piperazin-1-yl)butoxy]-1H-quinolin-2-one or a salt thereof, particle binders, and water for injection, the particle binders being sodium chloride and at least one member selected from the group consisting of polyoxyethylene sorbitan fatty acid esters and polyethylene glycols, wherein the 7-[4-(4-benzo[b]thiophen-4-yl-piperazin-1-yl)butoxy]-1H-quinolin-2-one or a salt thereof is a dihydrate of 7-[4-(4-benzo[b]thiophen-4-yl-piperazin-1-yl)butoxy]-1H-quinolin-2-one.

2. The injectable preparation according to claim 1, wherein secondary particles are formed by the aggregation of particles (primary particles) of the 7-[4-(4-benzo[b]thiophen-4-yl-piperazin-1-yl)butoxy]-1H-quinolin-2-one or a salt thereof, and the secondary particles have a mean-particle diameter (a mean secondary particle diameter) of 4 to 17 µm.

3. The injectable preparation according to claim 1 or 2, having a pH of 5 to 8.

4. A prefilled syringe that is prefilled with the injectable preparation according to claim 1 or 2.

5. The injectable preparation according to claim 1 or 2, wherein the particle binders are sodium chloride and a polyethylene glycol.

6. The injectable preparation according to claim 5, wherein the polyethylene glycol is macrogol 400 or macrogol 4000.

7. The injectable preparation according to claim 5, further comprising a polyoxyethylene sorbitan fatty acid ester.

8. The injectable preparation according to claim 7, wherein the polyoxyethylene sorbitan fatty acid ester is polyoxyethylene (20) sorbitan oleate.

9. The injectable preparation according to claim 2, wherein the particles of 7-[4-(4-benzo[b]thiophen-4-yl-piperazin-1-yl)butoxy]-1H-quinolin-2-one or a salt thereof have a mean primary particle diameter of 1 to 10 µm.

10. The injectable preparation according to claim 1 or 2, wherein the preparation releases an active ingredient in such a manner that its therapeutically effective blood concentration is maintained for at least one week.

11. A method for treating schizophrenia, bipolar disorder, or depression, the method comprising administering an effective amount of the injectable preparation according to claim 1 or 2.

12. The method according to claim 11, wherein the preparation is administered intramuscularly or subcutaneously.

13. A method for releasing an active ingredient in such a manner that its therapeutically effective blood concentration is maintained for at least one week comprising administering the injectable preparation according to claim 1 or 2.

* * * * *